US012233175B2

(12) United States Patent
Starkweather et al.

(10) Patent No.: US 12,233,175 B2
(45) Date of Patent: *Feb. 25, 2025

(54) MODULAR COMPONENTS, SYSTEMS, AND METHODS FOR DISINFECTING OBJECTS

(71) Applicant: UV-Concepts Inc., Englewood, CO (US)

(72) Inventors: Jeremy Starkweather, Castle Rock, CO (US); Jason Ylizarde, Conroe, TX (US); John Wynne, Cincinnati, OH (US); Brent Edmundowicz, Centennial, CO (US); Austin Starkweather, Denver, CO (US); Stefan L. Wenger, Columbine Valley, CO (US)

(73) Assignee: UV-Concepts Inc., Englewood, CO (US)

( * ) Notice: Subject to any disclaimer, the term of this patent is extended or adjusted under 35 U.S.C. 154(b) by 540 days.

This patent is subject to a terminal disclaimer.

(21) Appl. No.: 17/401,978

(22) Filed: Aug. 13, 2021

(65) Prior Publication Data

US 2022/0133924 A1 May 5, 2022

Related U.S. Application Data

(63) Continuation of application No. 16/860,141, filed on Apr. 28, 2020, now Pat. No. 11,090,399, which is a
(Continued)

(51) Int. Cl.
*A61L 2/10* (2006.01)
*A61L 2/14* (2006.01)
(Continued)

(52) U.S. Cl.
CPC .................. *A61L 2/10* (2013.01); *A61L 2/14* (2013.01); *A61L 2/202* (2013.01); *A61L 2/208* (2013.01);
(Continued)

(58) Field of Classification Search
CPC ................................. A61L 2/208; A61L 2/10
See application file for complete search history.

(56) References Cited

U.S. PATENT DOCUMENTS 2,375,226 A  5/1945 Higgins
4,743,059 A  5/1988 Legueu
(Continued)

FOREIGN PATENT DOCUMENTS

CN  1617747 A  5/2005
CN  102266166 A  12/2011
(Continued)

OTHER PUBLICATIONS

Boyce, J. M., "Modern technologies for improving cleaning and disinfection of environmental surfaces in hospitals," Boyce Antimicrobial Resistance and Infection Control (2016) 5:10, 10 pages.
(Continued)

*Primary Examiner* — Donald R Spamer
(74) *Attorney, Agent, or Firm* — COOLEY LLP

(57) ABSTRACT

Systems, apparatus, and methods are described for a disinfecting system formed of a plurality of modular units, wherein each modular unit is (1) coupleable to at least one other modular unit from the plurality of modular units and (2) includes an energy source from a plurality of energy sources. The plurality of energy sources can be configured to provide energy having an intensity capable of disinfecting a surface of the object located in a disinfecting area.

20 Claims, 27 Drawing Sheets

Related U.S. Application Data continuation of application No. PCT/US2019/038231, filed on Jun. 20, 2019.

(60) Provisional application No. 62/687,477, filed on Jun. 20, 2018.

(51) Int. Cl.
  *A61L 2/20* (2006.01)
  *A61L 2/28* (2006.01)

(52) U.S. Cl.
  CPC ............ *A61L 2/28* (2013.01); *A61L 2202/122* (2013.01); *A61L 2202/15* (2013.01); *A61L 2202/24* (2013.01)

(56) References Cited

U.S. PATENT DOCUMENTS

| | | | |
|---|---|---|---|
| 4,877,964 | A | 10/1989 | Tanaka et al. |
| 5,597,597 | A | 1/1997 | Newman |
| 5,958,336 | A | 9/1999 | Duarte |
| 6,165,526 | A | 12/2000 | Newman |
| 6,649,921 | B1 | 11/2003 | Cekic et al. |
| 6,730,923 | B1 | 5/2004 | May et al. |
| 7,490,578 | B1 | 2/2009 | Mottard |
| 7,791,044 | B1 | 9/2010 | Taylor et al. |
| 7,829,016 | B2 | 11/2010 | Deal et al. |
| 8,067,750 | B2 | 11/2011 | Deal |
| 8,536,541 | B2 | 9/2013 | Taylor et al. |
| 9,107,973 | B1 | 8/2015 | Robinson et al. |
| 9,492,577 | B1 | 11/2016 | Dayton |
| 9,682,161 | B2 | 6/2017 | Farren et al. |
| 9,687,575 | B2 | 6/2017 | Farren |
| 9,707,306 | B2 | 7/2017 | Farren |
| 10,046,073 | B2 | 8/2018 | Farren et al. |
| 10,255,466 | B2 | 4/2019 | Jinadatha |
| 10,272,167 | B2 | 4/2019 | Starkweather et al. |
| 10,603,394 | B2 | 3/2020 | Farren et al. |
| 11,033,643 | B2 | 6/2021 | Starkweather et al. |
| 11,090,399 | B2 * | 8/2021 | Starkweather ............ A61L 2/14 |
| 2002/0104271 | A1 | 8/2002 | Gallant |
| 2002/0168287 | A1 | 11/2002 | Eckhardt et al. |
| 2003/0133834 | A1 | 7/2003 | Karle |
| 2004/0052702 | A1 | 3/2004 | Shuman et al. |
| 2004/0170525 | A1 | 9/2004 | Ettlinger et al. |
| 2005/0063815 | A1 | 3/2005 | Pierson et al. |
| 2005/0201910 | A1 | 9/2005 | Shou et al. |
| 2006/0104858 | A1 * | 5/2006 | Potember ................ A61L 9/205 |
| | | | 422/123 |
| 2006/0186358 | A1 | 8/2006 | Couvillion |
| 2007/0012340 | A1 | 1/2007 | Jones et al. |
| 2008/0008620 | A1 | 1/2008 | Alexiadis |
| 2010/0007492 | A1 | 1/2010 | Ressler et al. |
| 2011/0073774 | A1 | 3/2011 | Taylor et al. |
| 2011/0274581 | A1 | 11/2011 | Davis |
| 2012/0062366 | A1 | 3/2012 | Pappu et al. |
| 2012/0181447 | A1 | 7/2012 | Yerby |
| 2012/0280147 | A1 | 11/2012 | Douglas |
| 2013/0175460 | A1 | 7/2013 | Farren |
| 2013/0216438 | A1 * | 8/2013 | Hill .......................... A61L 2/208 |
| | | | 422/187 |
| 2013/0256560 | A1 | 10/2013 | Yerby |
| 2014/0291552 | A1 | 10/2014 | Schumacher |
| 2014/0319375 | A1 | 10/2014 | Nelson et al. |
| 2015/0118107 | A1 | 4/2015 | Sunkara et al. |
| 2015/0205985 | A1 | 7/2015 | Jinadatha |
| 2015/0209459 | A1 | 7/2015 | Kreitenberg |
| 2015/0367008 | A1 * | 12/2015 | Romo ....................... A61L 2/10 |
| | | | 250/492.1 |
| 2016/0074546 | A1 | 3/2016 | Rizzone |
| 2017/0049915 | A1 | 2/2017 | Brais et al. |
| 2017/0260681 | A1 | 9/2017 | Gao et al. |
| 2018/0140727 | A1 | 5/2018 | Romo et al. |
| 2019/0347451 | A1 | 11/2019 | Jinedatha |
| 2019/0365938 | A1 | 12/2019 | Romo et al. |
| 2020/0078480 | A1 | 3/2020 | Starkweather et al. |
| 2020/0254122 | A1 | 8/2020 | Starkweather et al. |
| 2022/0105210 | A1 | 4/2022 | Starkweather et al. |
| 2022/0370671 | A1 | 11/2022 | Starkweather et al. |
| 2024/0139361 | A1 | 5/2024 | Starkweather et al. |

FOREIGN PATENT DOCUMENTS

| | | |
|---|---|---|
| CN | 106421836 A | 2/2017 |
| EP | 0755271 B1 | 1/2002 |
| IT | AT20120001 U1 | 11/2013 |
| WO | WO-2015167614 A1 | 11/2015 |
| WO | WO-2017205370 A1 | 11/2017 |
| WO | WO-2019246394 A1 | 12/2019 |
| WO | WO-2021133815 A2 | 7/2021 |

OTHER PUBLICATIONS

Examination Report No. 1 for Australian Application No. 2017269287, dated Jun. 4, 2021, 3 pages.
First Office Action for Chinese Application No. 201780042406.8, dated Sep. 25, 2020, 21 pages.
INAHTA Brief, "The clinical value of ultraviolet rays UV-C used for disinfection of endocavitary ultrasonography probes," Issue 2015/002 [Online], Retrieved from the Internet: URL: http://www.inahta.org/upload/2015/15002_Antigermix.pdf, 2015, 1 page.
Infection Control Today, "Technology Aids in HAI Prevention," [Online], Retrieved from the Internet: URL: https://www.infectioncontroltoday.com/hand-hygiene/technology-aids-hai-prevention, Jul. 23, 2009, 11 pages.
International Search Report and Written Opinion for International Application No. PCT/US2010/050837, mailed Oct. 22, 2010, 7 pages.
International Search Report and Written Opinion for International Application No. PCT/US2017/033996, mailed Nov. 15, 2017, 17 pages.
International Search Report and Written Opinion for International Application No. PCT/US2019/038231, mailed Oct. 18, 2019, 12 pages.
International Search Report and Written Opinion for International Application No. PCT/US2020/066644, mailed Jun. 30, 2021, 16 pages.
Ma, X. et al., "RFID-Based Healthcare Workflow Management in Sterile Processing Departments," Proceedings of the 2012 Industrial and Systems Engineering Research Conference (2012), 11 pages.
May, B. J. et al., "Nanowire LEDs Grown Directly on Flexible Metal Foil," Department of Electrical and Computer Engineering, The Ohio State University, 2016, 15 pages.
Myers, R. C. et al., "Ultraviolent Nanowire LEDs Grown Directly on Flexible Metal Foil," The Ohio State University Accelerator Award Presentation, Jul. 11, 2017, 6 pages.
Nanosonics, "trophon2 Consumables and Accessories," [Online], Retrieved from the Internet: https://www.nanosonics.com.au/trophon2-consumables-and-accessories/, 2017, 9 pages.
Office Action for Brazilian Application No. BR112018073966-9, dated May 10, 2021, 5 pages.
Office Action for European Application No. 17728013.8, mailed Aug. 14, 2020, 6 pages.
Office Action for European Application No. 19739474.5, mailed May 7, 2021, 8 pages.
Office Action for U.S. Appl. No. 15/602,771, mailed Aug. 31, 2018, 11 pages.
Office Action for U.S. Appl. No. 15/602,771, mailed Mar. 16, 2018, 9 pages.
Office Action for U.S. Appl. No. 16/390,536, mailed Feb. 11, 2020, 23 pages.
Office Action for U.S. Appl. No. 16/390,536, mailed Jul. 27, 2020, 27 pages.
Office Action for U.S. Appl. No. 16/860,141, mailed Dec. 16, 2020, 10 pages.
Office Action for U.S. Appl. No. 16/860,141, mailed Jun. 24, 2020, 13 pages.

(56) References Cited

OTHER PUBLICATIONS

Olympus, "Meet the demands of your busy schedule with the OER-Pro. 99% Uptime," [Online], Retrieved from the Internet: URL: https://medical.olympusamerica.com/customer-resources/cleaning-disinfection-sterilization/reprocessing-products/oer-pro, 2020, 6 pages.

Pletersek, A. et al., "Monitoring, Control and Diagnostics using RFID Infrastructure," J. Med. Syst. (2012) 36:3733-3739.

Quake Global, "Medical Equipment Management," [Online], Retrieved from the Internet: URL: https://www.quakeglobal.com/healthcare-rfid-equipment-management-processes, 2019, 3 pages.

Sarwar, A. T. M. G. et al., "Semiconductor Nanowire Light Emitting Diodes Grown on Metal: A Direction Towards Large Scale Fabrication of Nanowire Devices," Department of Electrical and Computer Engineering, The Ohio State University, 2015, 18 pages.

Seal Shield, "ElectroClave UV-C Disinfection with Mobile Device Management—SSECLAVE4B," [Online], Retrieved from the Internet: URL: http://www.sealshield.com/Products/Device-Management/ElectroClave-UV-Disinfection-Device-Manager.html, 2019, 4 pages.

Second Office Action for Chinese Application No. 201780042406.8, dated Jun. 9, 2021, 14 pages.

Swedberg, C., "RFID Enables Use of Non-synthetic Cleaner by Tracking Expirations," RFID Journal [Online], Retrieved from the Internet: URL: https://www.rfidjournal.com/articles/view?17574, Jun. 2018, 3 pages.

Xu, S. et al., "A RFID-based tracking system of endoscopes," 2011 4th International Conference on Biomedical Engineering and Informatics (BMEI), IEEE Xplore Digital Library [Online], URL: https://ieeexplore.ieee.org/document/6098686, Oct. 15-17, 2011, Shanghai, China.

Yedida, "Tag Archive for 'asset tracking," in Medical Devices and Technology, Bob on Medical Device Software, [Online], Retrieved from the Internet: URL: http://bobonmedicaldevicesoftware.com/blog/tag/asset-tracking/, Oct. 25, 2011, 5 pages.

Rejection Decision for Chinese Application No. 201780042406.8, dated Nov. 5, 2021, 15 pages.

Office Action for European Application No. 19739474.5, mailed Nov. 19, 2021, 8 pages.

Office Action for Brazilian Application No. BR112018073966-9, dated Dec. 6, 2021, 3 pages.

Partial European Search Report in European Application No. EP22152565.2, dated Aug. 25, 2012, 12 pages.

* cited by examiner

MODULAR COMPONENTS, SYSTEMS, AND METHODS FOR DISINFECTING OBJECTS

CROSS-REFERENCE TO RELATED APPLICATIONS

This application is a continuation of U.S. patent application Ser. No. 16/860,141, filed Apr. 28, 2020, titled "MODULAR COMPONENTS, SYSTEMS, AND METHODS FOR DISINFECTING OBJECTS," which is a continuation of International Patent Application No. PCT/US2019/038231, filed Jun. 20, 2019, titled "MODULAR COMPONENTS, SYSTEMS, AND METHODS FOR DISINFECTING OBJECTS," which claims priority to U.S. Provisional Patent Application No. 62/687,477, filed Jun. 20, 2018, titled "MODULAR COMPONENTS, SYSTEMS, AND METHODS FOR DISINFECTING OBJECTS," the disclosures of each of which is incorporated by reference herein.

TECHNICAL FIELD

The present disclosure relates generally to modular components, systems, and methods for disinfecting objects. More specifically, the present disclosure relates to disinfecting structures formed of modular units that include energy sources, such as light sources capable of emitting ultraviolet (UV) light, which can be used to disinfect objects, including equipment within a medical facility.

BACKGROUND

Disinfection of objects and spaces can reduce the transmission of pathogens. In medical facilities, disinfection of equipment, instruments, and other objects is important to prevent the spread of illnesses between individuals. Disinfection can be accomplished using, for example, UV light or other energy sources and/or disinfecting agents.

The effectiveness of a disinfection system can depend on the physical setting and/or method of disinfection. For example, with UV disinfection, it has been shown that intensity, proximity, and line of sight affect the ability of UV light emitted from a disinfection system to effectively eliminate pathogens on equipment and/or within spaces. But many existing UV disinfection systems, once installed within a medical setting, are stationary. For example, UV disinfection stations for disinfecting publicly-used equipment are described by Taylor et al. in U.S. Pat. Nos. 7,791,044 and 8,536,541, the disclosures of which are hereby incorporated by reference in their entirety. The stationary units described in these patents are particularly useful for disinfecting mobile equipment, such as shopping carts, wheelchairs, gurneys, etc. Because the units are stationary, however, the units may have limited applications, e.g., be designed for a specific space and/or type of equipment. When changes occur with the space and/or equipment, the disinfection units may need to be manually moved, adapted, or replaced.

In addition, existing systems capable of disinfecting larger scale objects and/or spaces may have dimensions that make them difficult to transport and deploy onsite. For example, such systems may have dimensions larger than standard size doorways and/or openings within a medical facility, and therefore require onsite construction and/or disassembly and reassembly to get through doorways and/or openings. Once the disinfection systems are assembled within a room or area, the systems may have limited mobility and/or adaptability. For example, such systems may be formed of a single, unitary structure that requires the entire system to be replaced (or a large portion of the system to be replaced) when individual, smaller components fail or require replacement over time. Such systems may also be difficult to move due to their large size and/or weight, be difficult to modify based on changes to equipment being disinfected and/or changes to the onsite location of the system, etc. These limitations and others can lead to significant costs, including downtime costs when a system is being installed, repaired, modified, and/or moved, and associated labor costs.

SUMMARY

Systems, apparatus, and methods described herein can overcome some of the disadvantages associated with existing disinfection systems. In particular, systems, apparatus, and methods described herein relate to disinfection systems having modular components.

In some embodiments, an apparatus includes a plurality of walls collectively defining a chamber sized to receive an object, where each wall from a set of walls from the plurality of walls is formed of a plurality of modular units, and each modular unit from the plurality of modular units is (1) coupleable to at least one other modular unit from the plurality of modular units and (2) includes an energy source from a plurality of energy sources. The at least one energy source from the plurality of energy sources can be configured to provide energy having an intensity capable of disinfecting a surface of the object when the object is received within the chamber.

In some embodiments, a kit includes components that can be assembled into a disinfection device. The kit can include a plurality of walls that can be assembled to collectively define a chamber sized to receive an object, where each wall from a set of walls from the plurality of walls is formed of a plurality of modular units, and each modular unit from the plurality of modular units is (1) coupleable to at least one other modular unit from the plurality of modular units and (2) includes an energy source from a plurality of energy sources. The at least one energy source from the plurality of energy sources can be configured to provide energy having an intensity capable of disinfecting a surface of the object when the object is received within the chamber.

In some embodiments, a method includes moving a plurality of modular units from a first location outside of an enclosed space to a second location inside the enclosed space through an opening, in which each modular unit from the plurality of modular units is sized to fit through the opening and includes an energy source; and assembling the plurality of modular units to form a structure that defines a chamber sized to receive an object, with each modular unit from the plurality of modular units arranged such that the energy source of that modular unit is disposed within the chamber and is configured to emit energy into the chamber to disinfect a surface of the object when the object is received within the chamber.

In some embodiments, a method includes positioning an object in a chamber of a disinfecting device including a portion formed from a plurality of modular units, the plurality of modular units including a plurality of energy sources and a plurality of fluid dispensers; energizing a set of energy sources from the plurality of energy sources to deliver energy at an intensity capable of disinfecting a surface of the object; and delivering, via a set of fluid dispensers from the plurality of fluid dispensers, a disinfecting agent into the chamber.

In some embodiments, an apparatus includes a plurality of modular units, in which each modular unit is (1) coupleable to at least one other modular unit from the plurality of modular units and (2) includes an energy source from a plurality of energy sources. A first set of energy sources from the plurality of energy sources can be configured to provide energy having an intensity capable of disinfecting a surface of the object when the surface of the object is disposed within a predefined distance from at least one of the plurality of modular units.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 5A and 5B depict a top view of the disinfection system, with a movable panel of the disinfection system shown in two different configurations. FIG. 5C depicts a front view of the disinfection system. And FIG. 5D depicts a side view of the disinfection system.

FIG. 9A depicts a view of the energy source covering a surface of a modular unit of the disinfection system, and FIG. 9B depicts a cross-sectional view of a portion of the modular unit, showing the energy source and other layers of the modular unit.

FIG. 14A depicts a side view of the disinfection system, and FIG. 14B depicts a top view of the disinfection system.

DETAILED DESCRIPTION

Systems, apparatus, and methods described herein relate to disinfecting structures formed at least in part of modular units and/or components. Systems, apparatus, and methods disclosed herein can be designed to disinfect objects or areas using energy sources that emit light (e.g., UV light) at distances and intensities capable of disinfecting various surfaces and materials and/or disinfecting agents (e.g., hydrogen peroxide, peracetic acid, electrolyzed water, atmospheric pressure plasma, polymeric guanidine, ozone, or combinations thereof) in amounts capable of disinfecting various surfaces and materials. Systems, apparatus, and methods disclosed herein can be designed to disinfect, e.g., reduce the count of microorganisms (e.g., bacteria, viruses, etc.) from surfaces of objects, to various degrees, depending on requirements (e.g., set by a hospital or organization) and/or the nature or means of disinfection (e.g., the type of disinfection used, an amount of time for the disinfection, the object being disinfected, the distance of the object from the disinfecting source, etc.). For example, disinfection systems disclosed herein can be capable of disinfecting an object to a particular level (e.g., cleaning, sanitizing, low-level disinfecting, high-level disinfecting, sterilizing), depending on the classification of that object based on its risk of infection. Embodiments of disinfection systems can be designed to select a level of disinfection based on a type of object and/or area being disinfected and operate to disinfect accordingly.

Although embodiments of the present disclosure are described with specific reference to systems and methods for disinfecting medical equipment (e.g., gurneys, wheelchairs, intravenous (IV) poles, dialysis machines, etc.) or medical enclosures (e.g., hospital rooms, surgery suites, diagnostic laboratories, etc.), it should be appreciated that such systems and methods may be used to disinfect a variety of items used or contacted by the public (e.g., shopping carts, shopping baskets, strollers, railings, door knobs, etc.) and a variety of enclosures (e.g., kitchens, public or private bathrooms, cafeterias, airplanes, buses, etc.).

Figure 1:
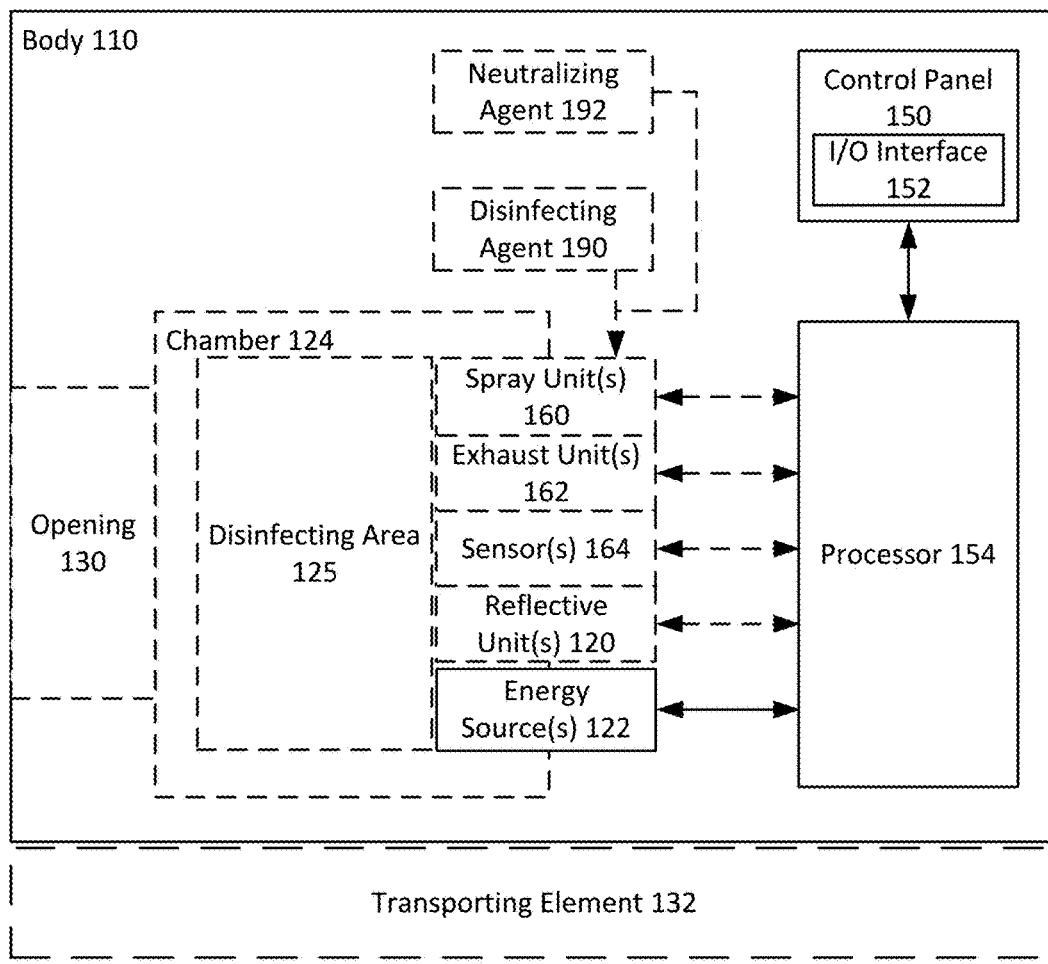
FIG. 1 schematically illustrates an example of a disinfection system, according to embodiments disclosed herein.

FIG. 1 is a high-level block diagram that schematically illustrates an example disinfection system 100, according some embodiments. Disinfection system 100 includes a body 110 and one or more energy source(s) 122. Disinfection system 100 can optionally include one or more reflective unit(s) 120, spray unit(s) 160, exhaust unit(s) 162, and/or sensor(s) 164.

Each energy source 122 is configured to emit energy that can be directed at objects disposed within a disinfecting area 125. Each energy source 122 can be configured to emit light, such as, for example, UV light at a wavelength of approximately 320-400 nanometers (nm) (i.e., UV-A light), UV light at a wavelength of approximately 290-320 nm (i.e., UV-B light), UV light at a wavelength of approximately 200-280 nm (i.e., UV-C light), and/or high-intensity narrow-spectrum (HINS) light (e.g., light at a wavelength of 405 nm). In some embodiments, a first set of energy source(s) 122 can be configured to emit a first type of energy (e.g., UV-B light) and a second set of energy source(s) 122 can be configured to emit a second type of energy (e.g., UV-C light). Each energy source 122 can include one or more mercury vapor bulbs or tubes, xenon gas bulbs or tubes, excimer bulbs or tubes, light emitting diodes (LED), light emitting nanoparticles, lasers, or other energy sources configured to emit light. For example, energy source(s) 122 may include light bulbs that are configured to emit at least 30 watts of UV energy (e.g., 36 watts of UV energy). As another example, energy source(s) 122 may include light emitting nanoparticles deposited or grown on a flexible conductive layer, as further described below in reference to FIGS. 9A and 9B. As another example, energy source(s) 122 can be configured to emit HINS light.

One or more energy source(s) 122 can be disposed within (e.g., removably or permanently) or near a reflective unit 120, such that energy emitted from the energy source(s) 122 can be directed into a disinfecting area 125 and/or an object disposed within the disinfecting area 125. Each reflective unit 120 can be formed of one or more reflective surface(s) capable of reflecting energy emitted from the energy source(s) 122. For example, reflective unit(s) 120 can have a curved reflective surface (e.g., a hyperbolic reflective surface) that directs energy emitted from the energy source(s) 122 in multiple directions into the disinfecting area 125. Alternatively, reflective unit(s) 120 can have a back surface and a plurality of reflective surfaces disposed off normal with respect to the back surface that direct energy emitted from energy source(s) in multiple directions into disinfecting area 125. Reflective unit(s) 120 can include reflective materials, such as, for example, mirrors, powder-coated materials or metal sheets, or Pebbletone™ and Hammertone™ finishes.

Energy source(s) 122 can be configured to emit energy having an intensity at a predefined distance (e.g., 100 µW/cm² at 1 meter) that is capable of disinfecting the surfaces of an object disposed within that predefined distance. In embodiments including reflective unit(s) 120, reflective unit(s) 120 can work in cooperation with energy source(s) 122 to ensure that a sufficient amount of energy for disinfecting an object is deposited on each surface of the object. Each surface of an object disposed within disinfecting area 125 can receive a collective amount of energy from various beams of energy (e.g., directly emitted by energy source(s) 122 and/or reflected via reflective unit(s) 120) that is sufficient to disinfect the surface, i.e., sufficiently reduce or eliminate pathogens disposed on the surface.

Disinfecting area 125 can be disposed adjacent to and/or within body 110 of disinfection system 100. For example, disinfecting area 125 can be located within a chamber 124 defined by body 110, or disinfecting area 125 can be an area that is adjacent to body 110. Body 110 can optionally define a chamber 124 for receiving an object requiring disinfecting. Chamber 124 can be sized to receive the object, and can include an opening 130 through which the object can be placed within chamber 124. The object can be, for example, medical equipment such as a gurney, a wheelchair, a pole to support bags of fluid for intravenous delivery (an IV pole), a medical cart, a mobile or portable computer station, a dialysis machine, an anesthesia machine, an electrocardiogram (ECG) machine, and/or other types of mobile medical items. Body 110 can include a wall, panel, and/or other structure capable of moving between an open configuration and a closed configuration to open and close the opening 130 of chamber 124. In some embodiments, chamber 124 can be designed to seal in energy and/or fluid, such that energy and/or fluid deposited within chamber 124 cannot exit chamber 124. Such sealing can prevent energy and/or fluid within the chamber 124 from affecting surrounding objects and/or persons, and allow use of certain types of disinfecting agents that may be harmful to surrounding objects and/or persons. Alternatively, in some embodiments, chamber 124 can be designed as an open chamber. For example, disinfection system 100 may include walls or surfaces that partially surround an open space (e.g., a disinfecting area 125). In such embodiments, any energy and/or disinfecting agents used with the disinfection system 100 may be ones that are not harmful to surrounding objects and/or persons. For example, a UV light source such as an excimer light source can be used to disinfect without objects in an open chamber without causing safety concerns.

In some embodiments, disinfection system 100 can be designed with or for use with a conveyor unit or other type of transport unit configured to move an object being disinfected through the disinfecting area 125. For example, disinfection system 100 can include one or more side panels or walls that are directed at the disinfecting area 125, and a transport unit (e.g., conveyor belt) can be configured to move the object being disinfected through the disinfecting area 125. In an embodiment, disinfection system 100 can include two side walls and a top wall (each formed of one or more modular units, as further described below) that encircle a space for receiving objects, and a bottom wall with a conveyor belt positioned thereon for moving the objects through the space. As objects are moved through the space encircled by the walls, the objects can be disinfected by one or more energy source(s) 122, reflective unit(s) 120, and/or spray unit(s) 160. An example of a disinfection system with a conveyor unit is described in more detail with reference to FIG. 11.

Disinfection system 100 can optionally include a transporting element 132. Transporting element 132 can be any combination of suitable components configured for movement, such as, for example, a wheel, a caster, a rail, a skid, a sled, a track, etc. Transporting element 132 can be provided along a bottom or base of disinfection system 100 and can enable movement of disinfection system 100, e.g., within a medical facility. Suitable examples of disinfection systems including transporting elements are disclosed in U.S. Patent Application Publication No. 2017/0340760, titled "System for disinfecting larger scale spaces and equipment," filed May 23, 2017, the disclosure of which is incorporated herein by reference.

Disinfection system 100 can operate according to one or more disinfecting modes. Disinfection system 100 can be designed to vary the disinfecting mode based on user inputs and/or sensed information regarding an object, e.g., the location of the object relative to one or more energy source(s) 122, the dimensions of the object, the type of object, the materials of the object, whether the object has hard or soft surfaces, the required level of disinfection associated with the object, etc. For example, disinfection system 100 can be configured to vary an amount of time of disinfection, use a subset of available energy source(s) 122, use specific types of energy source(s) 122 (when multiple types are available), adjust the configuration and/or positioning of reflective unit(s) 120, etc.

In some embodiments, disinfection system 100 includes spray unit(s) 160 (e.g. fluid dispensers) for applying one or more agents (e.g., disinfecting agent 190, neutralizing agent 192) to objects within disinfecting area 125. Disinfection system 100 can use spray unit(s) 160 to apply the agents to further disinfect and/or treat an object being disinfected. Spray unit(s) 160 can be configured to dispense the agents in a liquid spray and/or a vapor/gas. In some embodiments, spray unit(s) 160 can be adjusted (e.g., via processor 154 and/or control panel 150) to change a direction and/or spray profile of a sprayed substance. For example, spray unit(s) 160 can include one or more nozzles with openings that can be adjusted to vary an amount of liquid and/or vapor that is sprayed, the profile of the produced spray, and/or a direction of the produced spray. In some embodiments, spray unit(s) 160 can apply an electrostatic charge to the sprayed agent to encourage droplets of the agent to spread out more evenly and adhere to the neutral or negative charged surfaces of objects. In some embodiments, spray unit(s) 160 can be connected to a source of pressurized gas that can be used to generate aerosolized streams of disinfecting agent 190 and/or neutralizing agent 192.

In some embodiments, disinfection system 100 can be configured to use one or more energy source(s) 122 to disinfect an object, as well as one or more spray unit(s) 160 to apply a disinfecting agent 190 and/or a neutralizing agent 192 to the object. By disinfecting with energy source(s) 122 and disinfecting agents 190, disinfection system 100 can target different types surfaces and/or different types of pathogens. For example, energy source(s) 122 capable of emitting UV-C light have been shown to be effective at killing pathogens on hard surfaces, while a disinfecting agent 190 such as hydrogen peroxide has been shown to be effect at disinfecting soft surfaces. Therefore, disinfection system 100 may use both energy source(s) 122 and disinfecting agents 190 to disinfect an object having hard and soft surfaces. Disinfection system 100 may run a first disinfection cycle using energy source(s) 122 that emit UV-C light (e.g., a UV-C cycle) and a second disinfection cycle using the disinfecting agents 190 (e.g., a vapor cycle), sequentially or simultaneously. In an embodiment, disinfection system 100 can be configured for photocatalytic disinfection. For example, disinfection system, via spray unit(s) 160, can apply a light-activated photosensitizer (e.g., titanium dioxide) to surfaces and use UV light and/or electromagnetic radiation emitted by one or more energy source(s) 122 to activate the photosensitizer and disinfect the surfaces.

Disinfecting agent 190 can include, for example, hydrogen peroxide, peracetic acid, electrolyzed water, atmospheric pressure plasma, polymeric guanidine, or ozone. Neutralizing agent 192 can be configured to reduce degradation of the object caused by the use of a disinfecting agent 190 and/or a particular type of energy source 122. For example, neutralizing agent 192 can be applied before, during, and/or after activing the energy source(s) 122 and/or applying the disinfecting agent 190 to treat the surfaces of the object being disinfected, such that the object degrades less over time. Neutralizing agent 192 can also be configured to reduce the risk of harmful contact between a human and a disinfecting agent 190. An example of a suitable neutralizing agent 192 can be water. Disinfecting agent 190 and/or neutralizing agent 192 can be delivered as a liquid spray and/or vapor.

Disinfection system 100 can optionally include exhaust unit(s) 162 configured to vent away air from disinfecting area 125 (e.g., to vent air out of chamber 124) and/or supply clean air to disinfecting area 125 (e.g., to supply clean air into chamber 124). Exhaust unit(s) 162 can be used in conjunction with spray unit(s) 160 to vent away air and/or vapors carrying disinfecting agent 190 and/or neutralizing agent 192. When disinfection system 100 is used with spray unit(s) 160 and/or exhaust unit(s) 162, body 110 can define a sealed chamber (e.g., chamber 124) such that air containing disinfecting agents, neutralizing agents, and/or other substances can be sealed within the chamber and removed via exhaust unit(s) 162, without exposing a user outside of the disinfecting area 125 to such air.

In some embodiments, disinfection system 100 includes one or more sensor(s) 164 for collecting information regarding components of disinfection system 100, objects within and/or near disinfection system 100, and/or other information that may affect the operation of disinfection system 100. Sensor(s) 164 can be coupled and/or integrated into a panel or wall of disinfection system 100 or another component of disinfection system 100 (e.g., an energy source 122, a reflective unit 120, a spray unit 160, or an exhaust unit 162). Sensor(s) 100 can include, for example, motion sensors, image capture devices (e.g., cameras), light sensors, temperature sensors, pressure sensors, sound detectors, ozone sensors, etc. For example, sensor(s) 164 can include at least one motion sensor capable of detecting movement within and/or near disinfecting area 125 to determine whether a user may be harmed by energy, disinfecting agents, and/or other components of disinfection system 100. In some embodiments, sensor(s) 164 can be configured to detect and/or determine information about objects within disinfecting area 125. For example, sensor(s) 164 can include image capture devices that can capture images of objects within disinfecting area 125 and determine the object type, dimensions of the objects, distance and/or positioning of the objects relative to energy source(s) 122 and/or spray unit(s) 160, or other information regarding the objects. Alternatively or additionally, sensor(s) 164 can include weight sensors, light sensors, etc. located on a base or floor associated with disinfection system, which can measure the weight, position, size, and/or orientation of objects within disinfecting area 125. Disinfection system 100 can use this information to determine how to disinfect the objects. In some embodiments, sensor(s) 164 can be coupled to and/or integrated into an energy source 122, reflective unit 120, and/or a spray unit 160, and be configured to monitor the operation of such components. For example, sensor(s) 164 can monitor temperatures and/or moisture levels associated with such components, which can be used to confirm and/or modify disinfecting procedures.

In some embodiments, sensor(s) 164 can include a radio frequency identification (RFID) sensor, Quick Response (QR) reader, or other type of suitable sensor for identifying a user of the disinfection system 100 and/or objects placed within the disinfecting area 125. Such sensor(s) 164 can be used to control access to and/or use of the disinfection system 100, and/or to log information associated with use of the disinfection system 100. For example, a RFID sensor can be configured to read a badge or other identifying card and/or device of a user to permit access by the user to the disinfection system 100. A RFID sensor or a QR reader can be configured to read a tag (e.g., a RFID tag or QR code) located on an object placed in the disinfecting area 125 to identify the type of object. An onboard processor (e.g., processor 154, described below) or another device in communication with the sensor(s) 164, e.g., via a wired or wireless connection, can log the disinfections performed by the disinfection system 100. In some embodiments, sensor(s) 164 can also detect when maintenance of the disinfection system 100 may be required, e.g., when a sensor 164 detects that a particular energy source 122 may no longer be functional.

Disinfection system 100 can include a control panel 150 with an input/output (I/O) interface 152. Control panel 150, via I/O interface 152, can be configured to receive and process user inputs and/or monitor the operations and functions of disinfection system 100. The control panel 150 can be electrically coupled to a processor 154, which can be used to control one or more components of disinfection system 100. Processor 154 can be any suitable processing device configured to execute functions associated with disinfection system 100. For example, processor 154 can be configured to activate one or more energy source(s) 122. In embodiments where disinfection system 100 includes reflective unit(s) 120, processor 154 can be electrically coupled to one or more reflective unit(s) 120 and be configured to move (e.g., rotate, translate, etc.) the reflective unit(s) 120 to control the direction that energy is reflected, e.g., to target a surface of an object and/or specific area within disinfecting area 125. In embodiments where disinfection system 100 includes sensor(s) 164, processor 154 can be electrically coupled to one or more sensor(s) 164 and be configured to receive information from the sensor(s) 164 (e.g., information regarding objects within disinfecting area 125, one or more components of disinfection system 100, and/or an environment around disinfection system 100). Processor 154 can be configured to select specific disinfection modes (e.g., disinfection type or cycle), deactivate the disinfection system 100 (e.g., in cases where a user may be harmed by disinfection procedures), change a disinfection step, and/or provide an alert or status update (e.g., an audio and/or visual alert, or an electronic alert), based on the information received from the sensor(s) 164. Processor 154 can be, for example, one or more of a general purpose processor, a Field Programmable Gate Array (FPGA), an Application Specific Integrated Circuit (ASIC), a Digital Signal Processor (DSP), and/or the like. Disinfection system 100 can also include an onboard power source (e.g., a battery) and/or be coupled to a power source (e.g., be plugged into a wall socket). I/O interface 152 can include a user interface with one or more components that are configured to receive inputs and/or present outputs to users and/or user devices. For example, the user interface can include a display device (e.g., a display, a touch screen, etc.), an audio device (e.g., a microphone, a speaker), a keyboard, a scanner or reader (e.g., a radio-frequency identification (RFID) reader, a near-field communication (NFC) reader, etc.), etc.

In some embodiments, disinfection system 100 can be connected to a network (e.g., a local area network (LAN), a wide area network (WAN), a virtual network, a telecommunications network) implemented as a wired network and/or wireless network and be configured to communicate with other devices coupled to the network, e.g., another disinfection system 100, a server, or other compute devices. Disinfection system 100 can be configured to receive and send information via the network, including, for example, information regarding the operation of and/or disinfections performed by disinfection system 100. In some embodiments, disinfection system 100, via the network, can be connected to a remote control panel or system through which a user can remotely control disinfections system 100. In some embodiments, disinfection system 100 can be connected to a cloud network that hosts one or more other applications that can interface with disinfection system 100 to provide other service(s). For example, disinfection system 100 can be connected to a remote server that tracks the object(s) that have been disinfected by the disinfection system 100, and can provide this information to administrator and/or for reporting purposes. In some embodiments, disinfection system 100 can also report information regarding disinfected object(s) to cloud-based applications and/or devices that facilitate real-time updates to local staff within a medical facility (e.g., updates at a computer and/or electronic indicator tags on disinfected object(s)).

Disinfection system 100 can be a unitary structure, or disinfection system 100 can be implemented as multiple structures located in the vicinity of one another. In some embodiments, disinfection system 100 can be formed of modular units that can be assembled together to form disinfection system 100, as further described below.

Figure 2A:
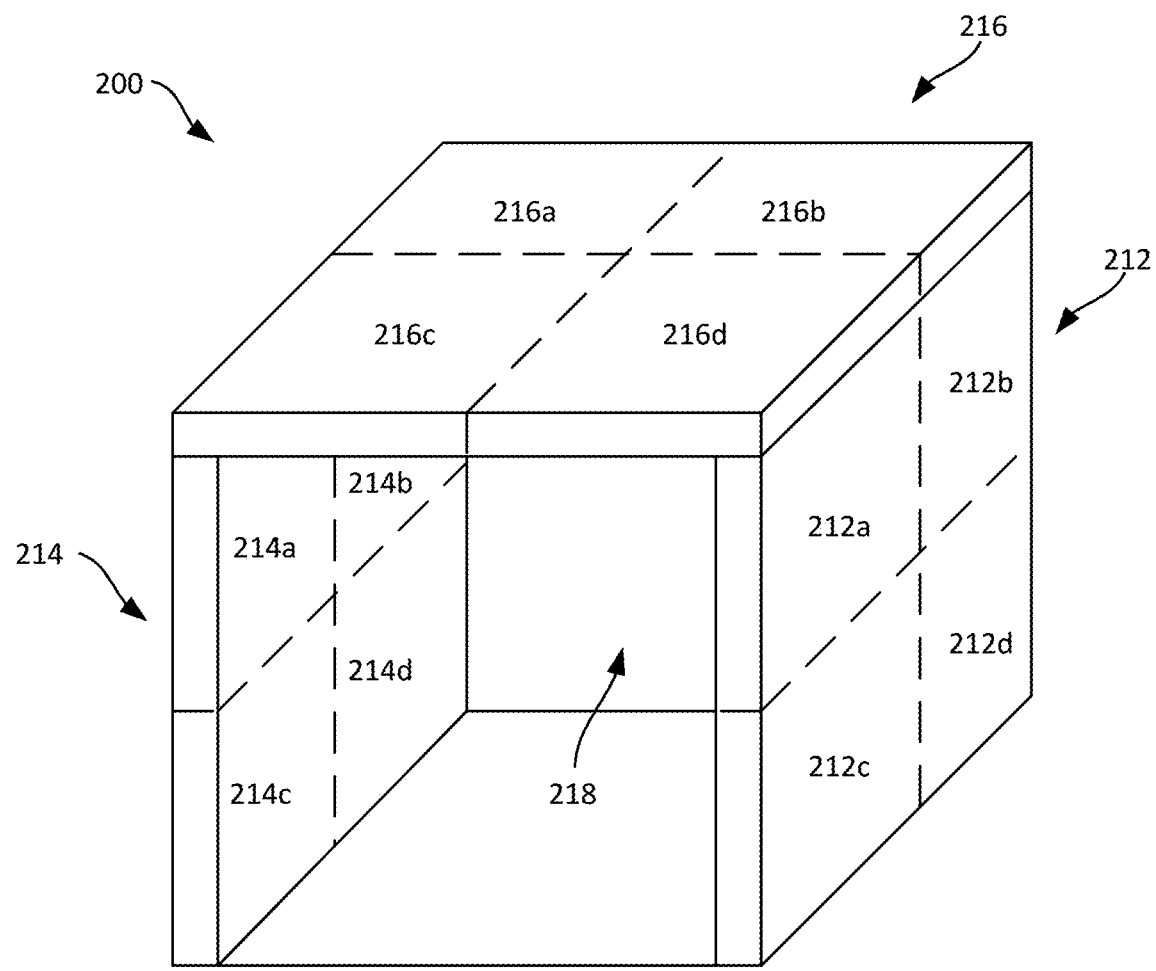
FIG. 2A schematically illustrates an example of a disinfection system including modular units, according to embodiments disclosed herein.

FIG. 2A depicts an example disinfection system 200, according to embodiments disclosed herein. Disinfection system 200 can be formed of a plurality of modular units. Disinfection system 200 includes side walls 212, 214, a top wall 216, and a back wall 218. In some embodiments, disinfection system 200 can also include additional walls, e.g., a floor or bottom wall and/or a front door or wall (not depicted). Each wall 212, 214, 216, 218 can be formed of one or more modular units. For example, wall 212 can optionally be formed of four modular units 212*a*, 212*b*, 212*c*, 212*d*; wall 214 can optionally be formed of four modular units 214*a*, 214*b*, 214*c*, 214*d*; and wall 216 can be formed of four modular units 216*a*, 216*b*, 216*c*, 216*d*. Alternatively, each of walls 212, 214, 216 can be formed of a single modular unit. Modular units 212*a*, 212*b*, 212*c*, 212*d* can be similar to one another and include the same components (e.g., energy source(s), reflective unit(s), spray unit(s), etc.) and/or also be similar to other modular units of other walls, e.g., modular units 214*a*, 214*b*, 214*c*, 214*d* and/or modular units 216*a*, 216*b*, 216*c*, 216*d*. Each modular unit can be designed to be interchangeable with one or more other modular units, e.g., modular unit 212*a* can be interchangeable with any one of modular units 212*b*, 212*c*, 212*d* and/or other modular units, such as one or more of modular units 214*a*, 214*b*, 214*c*, 214*d*, 216*a*, 216*b*, 216*c*, 216*d*.

Each modular unit can be manufactured and/or assembled at a manufacturing facility and transported to a location for onsite assembly into disinfection system 200. Transportation costs can be reduced by transporting the modular units separately to an onsite location. Individual modular units can be dimensioned to fit through standard sized doorways and openings within a building, such as, for example, a medical facility. Each modular unit can also weigh and/or be dimensioned such that a human can directly lift and/or move the units, or use standard moving tools to lift and/or move the units, such as, for example, a dolly, a lift, a moving cart, etc.

Each modular unit can be coupled to the modular units adjacent to it via suitable fastening elements (e.g., mechanical fasteners, magnets, adhesives, etc.). In some embodiments, modular units can include built-in connectors for quick coupling and assembly, e.g., snap-on connectors, magnetic connectors, etc.

While disinfection system 200 is depicted as a box-shaped structure, in other embodiments, disinfection system can have a different shape, e.g., a spherical shape, a pyramidal shape, a cylindrical shape, etc.

Figure 2B:
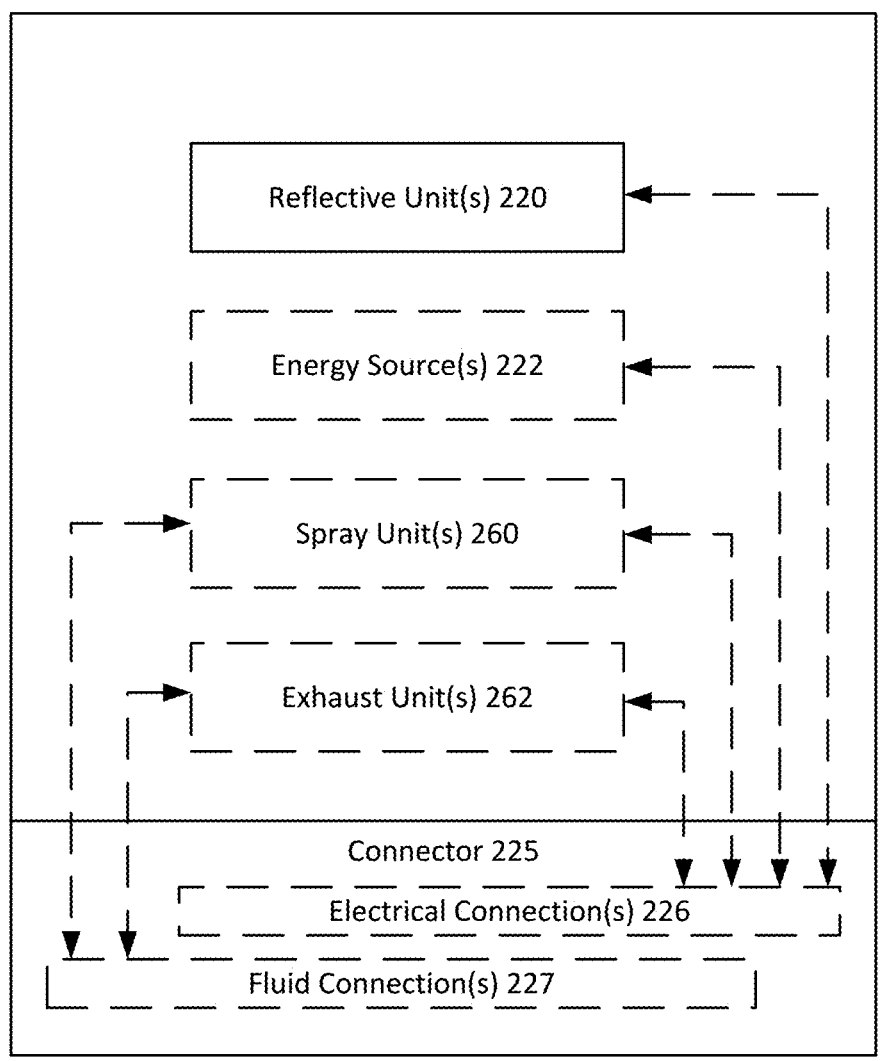
FIG. 2B schematically illustrates an example of a modular unit of a disinfection system, according to embodiments disclosed herein.

FIG. 2B provides a schematic view of modular unit 212a, which can be similar to and/or the same as other modular units depicted in FIG. 2A (e.g., modular units 212b, 212c, 212d, 214a, 214b, 214c, 214d, 216a, 216b, 216c, 216d). Modular unit 212a can include at least one reflective unit 220 and can optionally include one or more energy source(s) 22, spray unit(s) 260, and/or exhaust unit(s) 262. Reflective unit 220 can be similar to reflective unit 120, as described above. For example, reflective unit 220 can have one or more surfaces configured to reflect energy emitted by energy sources disposed on modular unit 212a and/or other modular units (e.g., modular units 212b, 212c, 212d, 214a, 214b, 214c, 214d, 216a, 216b, 216c, 216d). When modular unit 212a is assembled in disinfection system 200, reflective unit 220 can be disposed on an inner surface of wall 212, such that reflective unit 220 can be configured to direct energy emitted by energy sources into a chamber defined by walls 212, 214, 216. In some embodiments, reflective unit 220 can be adjusted, e.g., manually and/or automatically, to change the direction that it directs energy into the chamber defined by walls 212, 214, 216. Reflective unit 220 can have a concave shape (e.g., a hyperbolic shape) that can spread and reflect energy into the chamber, or have multiple reflective surfaces that are angled with respect to one another to spread and reflect light into the chamber. In some embodiments, reflective unit 220 can be implemented as a reflective coating that can cover a portion or all of an inner facing surface of modular unit 212a. In other embodiments, reflective unit 220 can be implemented as a one or more reflective surface mounted on beams or other support structures attached to an inside surface of modular unit 212a.

Energy source(s) 222 can be similar to energy source(s) 122. For example, each energy source 222 can be configured to emit energy, such as, for example, UV light or HINS light. When modular unit 212a is assembled in disinfection system 200, energy source(s) 222 can be disposed on an inner surface of wall 212, such that energy emitted by energy source(s) 222 can be directed into the chamber defined by walls 212, 214, 216. In some embodiments, energy source(s) 222 can emit light that is predominantly UV-C light (e.g., at least 75% of which is UV-C light).

While reflective unit(s) 220 and energy source(s) 222 are described with reference to a modular unit 212a, one or more reflective unit(s) 220 and/or energy source(s) 222 can be disposed on other modular units, e.g., one or more of modular units 212b, 212c, 212d, 214a, 214b, 214c, 214d, 216a, 216b, 216c, 216d, or on other surfaces of disinfection system 200 (e.g., back wall 218 and/or a bottom wall or floor). Collectively, reflective unit(s) 220 and/or energy source(s) 222 disposed on the modular units, walls, and/or other portions of disinfection system 200 can ensure that an adequate amount of energy reaches each surface of an object that is located within the chamber, such that the object can be disinfected using the emitted energy. More specifically, reflective unit(s) 220 and/or energy source(s) 222 can be disposed in any suitable location, orientation, configuration, size, and/or number such that an object within the chamber defined by walls 212, 214, 216 is exposed to energy at sufficient intensities (e.g., at least 100 $\mu W/cm^2$ at 1 meter) for a sufficient amount of time to enable disinfection.

Spray unit(s) 160 can be similar to spray unit(s) 160. For example, spray unit(s) 260 can be configured to deliver one or more agents (e.g., disinfecting agents, neutralizing agents) into the chamber. When modular unit 212a is assembled in disinfection system 200, spray unit(s) 260 can be disposed on an inner surface of wall 212, such that spray unit(s) 260 can direct one or more agents at an object located within the chamber. Spray unit(s) 260 can be configured to deliver the agents as a liquid spray and/or vapor. In some embodiments, spray unit(s) 260 can be configured to electrically charge droplets of the agent such that the droplets are predisposed to evenly distribute and/or adhere to the surfaces of an object within the chamber. Modular unit 212a can include fluid connection(s) 227 that are coupled to spray unit(s) 260 and can provide fluid communication between spray unit(s) 260 and a source of an agent (e.g., a fluid reservoir). Fluid connection(s) 227 can include ports and/or channels integrated into, coupled to, and/or coupleable to the modular unit 212a.

Exhaust unit(s) 262 can be similar to exhaust unit(s) 162. For example, exhaust unit(s) 262 can be configured to circulate air into and/or out of the chamber. For example, exhaust unit(s) 262 can be configured to vent air out of chamber, e.g., with a fan, by applying a vacuum or suction, or other suitable means. Additionally or alternatively, exhaust unit(s) 262 can circulate clean air into the chamber, e.g., via a fan, air pump, or other suitable means. Exhaust unit(s) 262 can be coupled to fluid connection(s) 227, which provide an inlet and/or outlet path for air from the chamber. In some embodiments, exhaust unit(s) 262, via fluid connection(s) 227, can vent air through a filtration and/or air purification system, which can clean and/or disinfect the air for recirculation through other fluid channels and/or exhaust unit(s) 262 back into the chamber.

Modular unit 212a can optionally include electrical connection(s) 226. Electrical connection(s) 226 can be coupled to one or more of reflective unit(s) 220, energy source(s) 222, spray unit(s) 260, and/or exhaust unit(s) 262, to connect those components to a power source and/or control unit (e.g., an onboard or off-board control unit, including, for example, a processor and/or control panel). The control unit (not depicted) can be used to control the operation of one or more of reflective unit(s) 220, energy source(s) 222, spray unit(s) 260, and/or exhaust unit(s) 262. For example, the control unit can be used to selectively activate, move, and/or adjust one or more of one or more of reflective unit(s) 220, energy source(s) 222, spray unit(s) 260, and/or exhaust unit(s) 262. In some embodiments, the control unit can be coupled to one or more sensors for detecting information about the objects within chamber, the surrounding environment, and/or a user of the disinfection system 200.

Modular unit 212a can include a connector 225, which can be used to couple modular unit 212a to other modular unit(s) (e.g., modular unit 212b or 212c). In some embodiments, connector 225 can include electrical connection(s) 226 and/or fluid connection(s) 227, which can be coupled to one or more of reflective unit(s) 220, energy source(s) 222, spray units) 260, and/or exhaust unit(s) 262. Connector 225 can be disposed on a side of modular unit 212a, such that connector 225 can be configured to couple to a connector on an adjacent modular unit (e.g., modular unit 212b or 212c) when the two modular units are attached to one another. In some embodiments, connector 225 can be designed as a snap-on connector that can engage with a corresponding connector located on an adjacent modular unit. Connector 225, via a network of connections (e.g., including additional connectors, electrical connection(s), and/or fluid connection(s)) through modular units, can be coupled to an air ventilation system, an air filtration system, a source of disinfecting agent and/or neutralizing agent, a control unit, power source, etc.

Figure 3A:
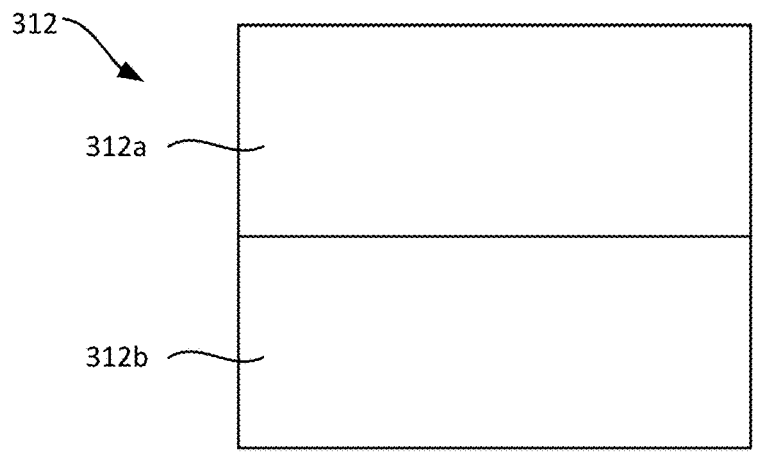
FIGS. 3A-3C schematically illustrate different configurations of modular units of disinfection systems, according to embodiments disclosed herein.
Figure 3B:
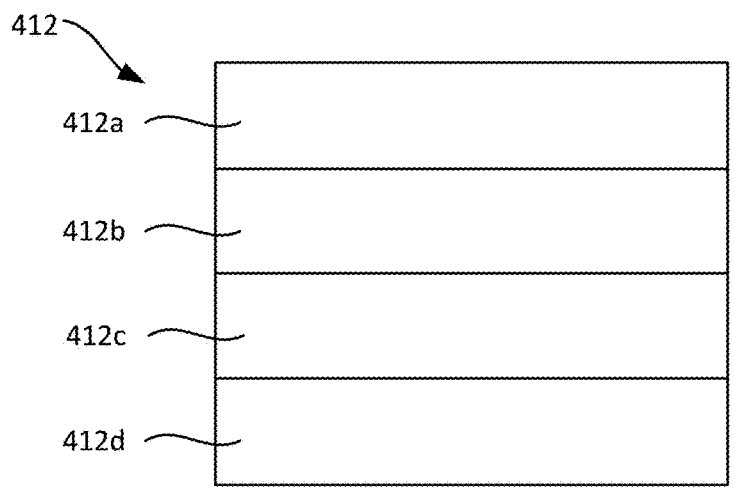
Figure 3C:
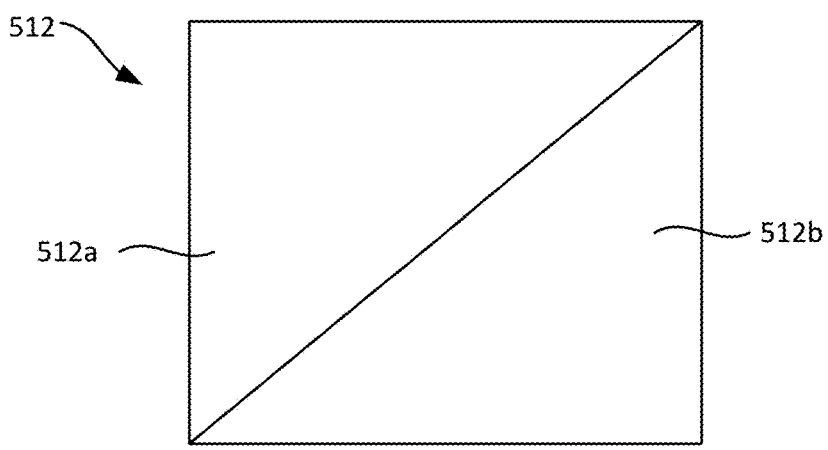

While disinfection system 200 is depicted as having walls that can be formed of a single modular unit or, optionally, formed of four modular units placed in a two-by-two arrangement (e.g., wall 212 being formed of four modular units 212a, 212b, 212c, 212d), other disinfection systems can include walls with different arrangements and/or configurations (e.g., shapes, sizes, etc.) of modular units. For example, FIG. 3A depicts a wall 312 formed of two modular units 312a, 312b that are rectangular-shaped positioning in a two-by-one arrangement (i.e., with modular unit 312a positioned above modular unit 312b). FIG. 3B depicts a wall 412 formed of four modular units 412a, 412b, 412c, 412d that are rectangular-shaped and positioned in a four-by-one arrangement. FIG. 3C depicts a wall 512 formed of two modular units 512a, 512b, each having a triangular shape and coming together to form a rectangular shaped wall. Different arrangements and/or configurations of modular units can be used, e.g., to accommodate differently shaped components (e.g., energy sources, reflective units, spray units, exhaust units) and/or due to space limitations (e.g., during shipping and transport to an onsite location). In some embodiments, modular units can be designed with longer coupling surfaces (e.g., for coupling to adjacent modular units), such that more connections between the two modular units can be accommodated and/or more stability can be provided via the coupling.

Figure 4:
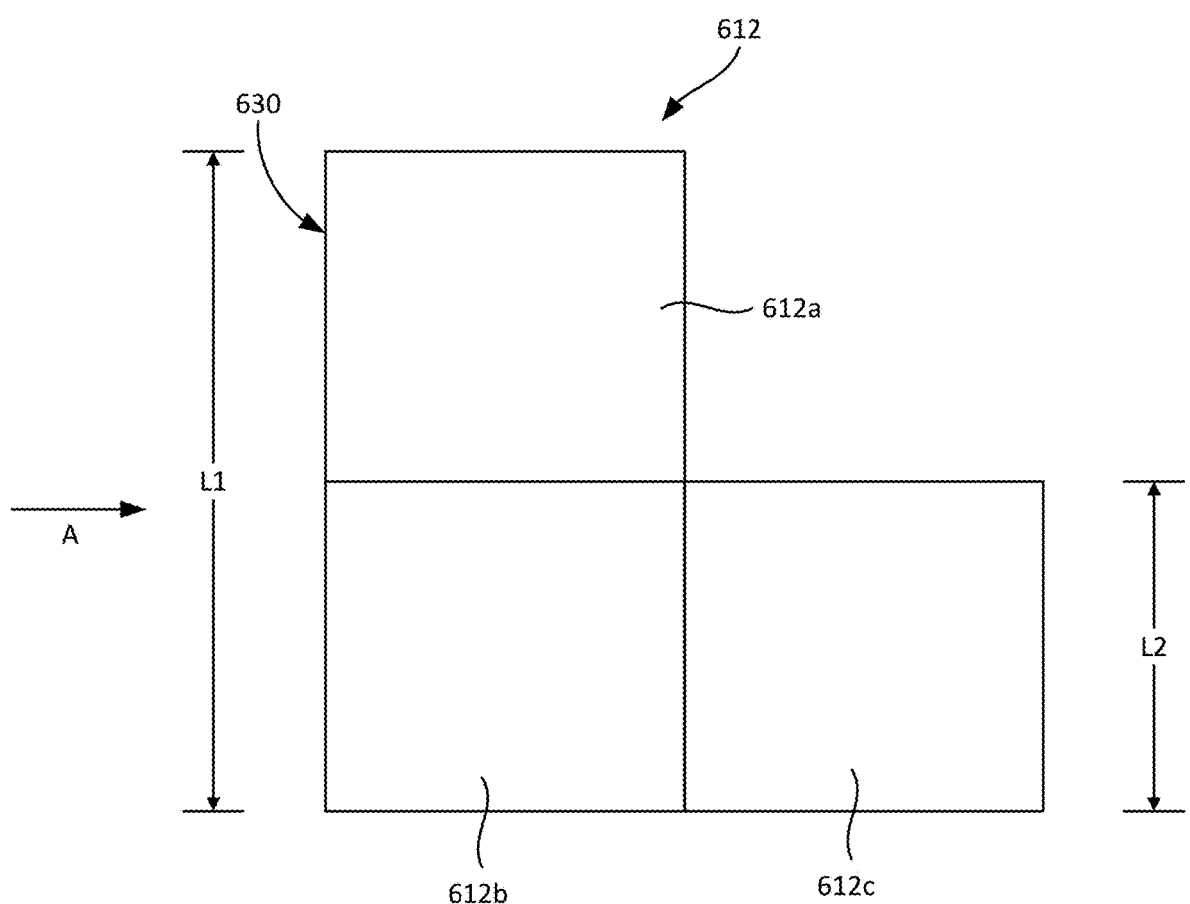
FIG. 4 schematically illustrates an example of a side panel of a disinfection system formed of modular units, according to embodiments disclosed herein.

FIG. 4 depicts another arrangement of modular units forming a wall 612 of a disinfection system. As depicted, wall 612 is formed of three modular units 612a, 612b, 612c. Modular units 612a, 612b, 612c can similar to and/or the same as one another. Modular units 612a, 612b, 612c can be arranged in a L-shaped configuration, such that wall 612 can have ends with varying lengths. Specifically, wall 612 can have a first end with a length L1 and a second end with a length L2, where length L1 is equal to the combined length of two modular units 612a, 612b and length L2 is equal to the length of a single modular unit 612c. When wall 612 is assembled in a disinfection system, wall 612 can define a chamber that has regions with varying height such that it can receive a similarly shaped object. For example, the chamber can be configured to receive a gurney with an attached IV pole such that the height of the IV pole can be accommodated by the taller region defined by modular units 612a, 612b. Other arrangements and/or configurations of modular units can be used to construct disinfection systems capable of receiving objects having other sizes and/or shapes.

Disinfection systems having a modular design can have improved customizability, adaptability, and/or serviceability. For example, individual modular units can be designed to be interchangeable with one another, and can be assembled together in a number of different ways to form differently shaped and/or sized disinfection systems. Depending on a user's disinfection needs and/or space limitations, the user can select from several different types of modular units, and can assemble those modular units in various ways to define differently sized and shaped disinfection areas and/or chambers. When a particular component of a modular unit requires maintenance and/or repair, that modular unit can be replaced without requiring the entire disinfection system to be serviced and/or replaced, thereby reducing repair costs and/or downtime. Additionally, when improvements to modular units are available (e.g., a new design of a particular modular unit becomes available), existing disinfection systems can be outfitted with the new modular units by replacing old units with the new ones without requiring a full redesign and/or replacement of the system.

Figure 5A:
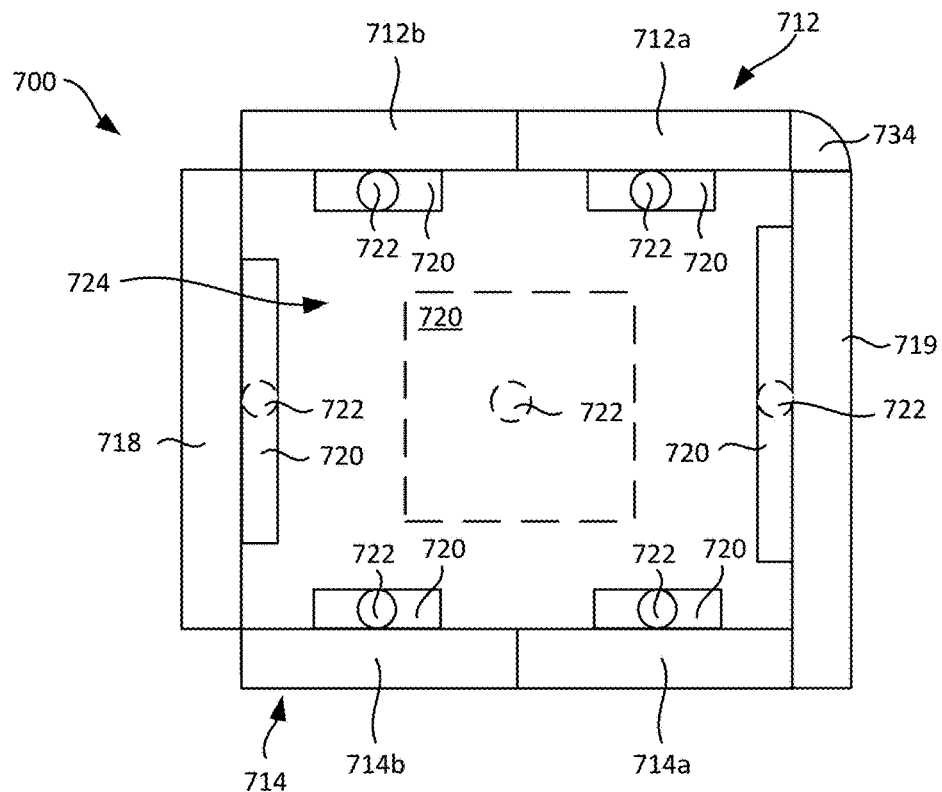
FIGS. 5A, 5B, 5C, and 5D schematically illustrate different views of an example disinfection system including modular units, according to embodiments disclosed herein.
Figure 5B:
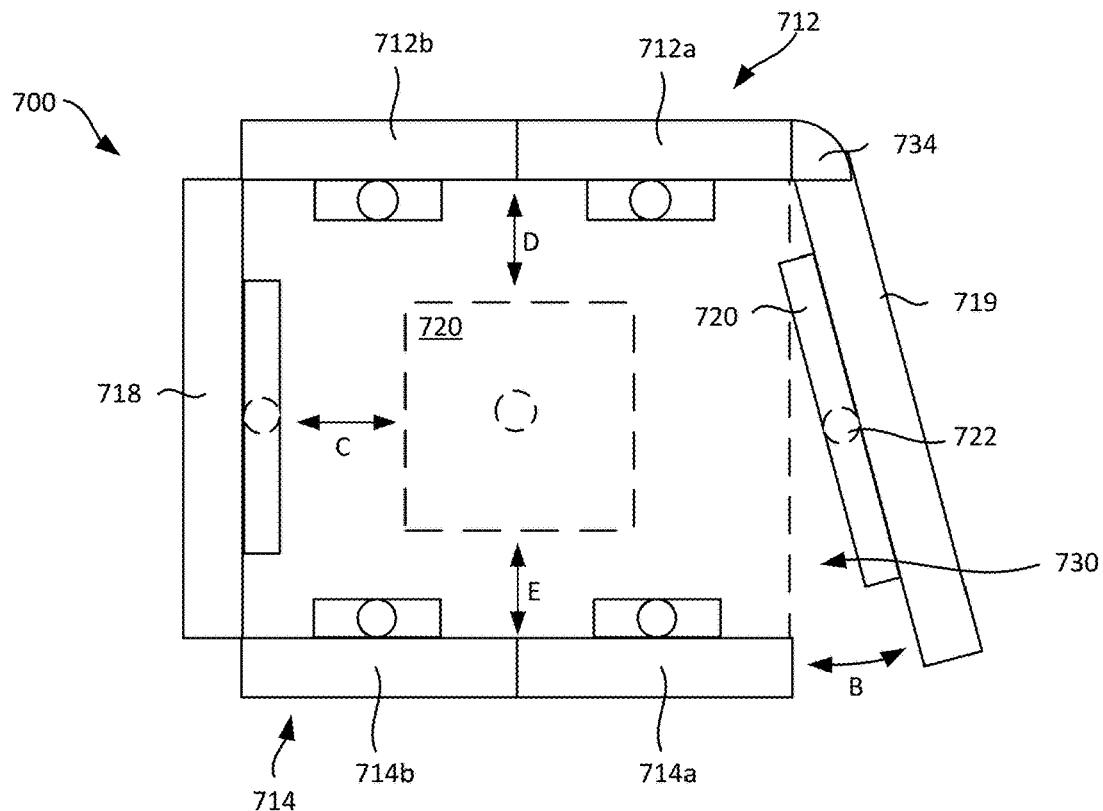
Figure 5C:
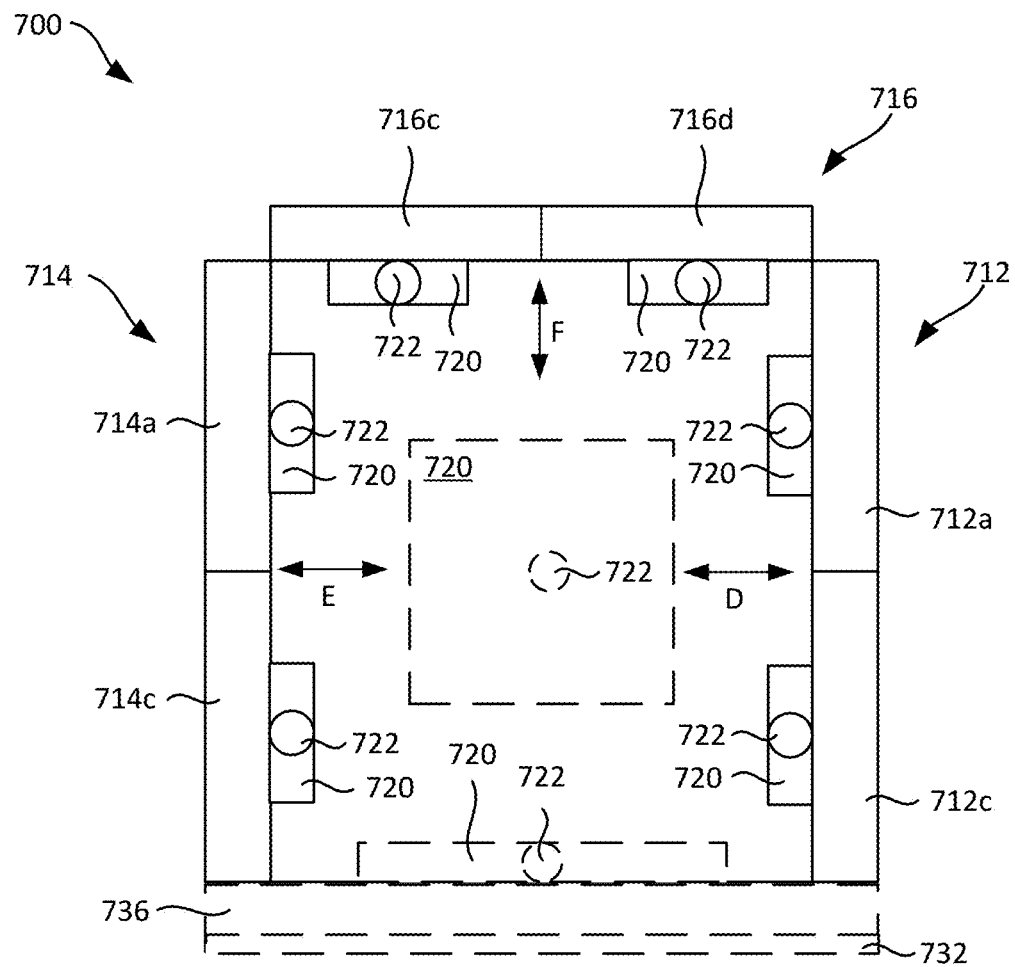
Figure 5D:
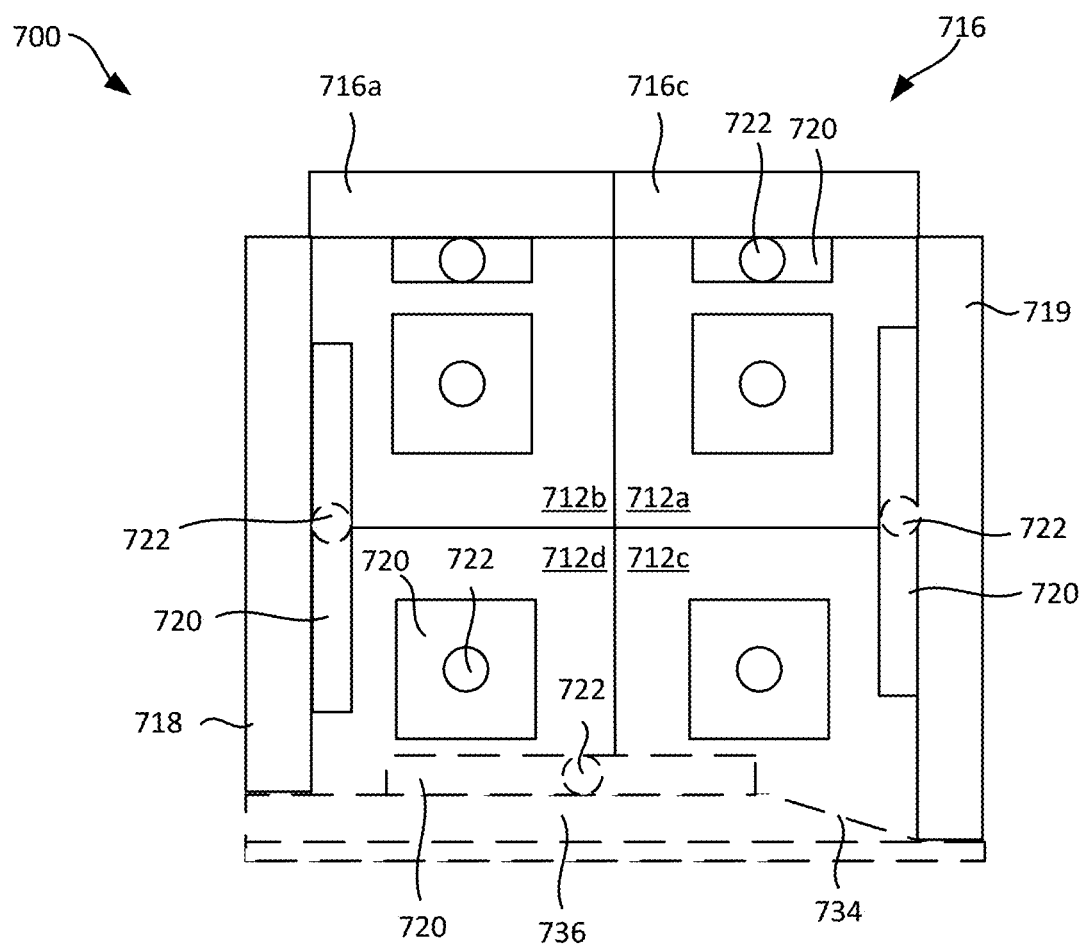

FIGS. 5A, 5B, 5C, and 5D schematically illustrate an example disinfection system 700, according to some embodiments. Disinfection system 700 includes a plurality of walls, i.e., side walls 712, 714, a top wall 716, a back wall 718, a front wall 719, and optionally a base or bottom wall 736. FIGS. 5A and 5B depict a top view of disinfection system 700, with the top wall 716 removed to show interior features of the system. FIG. 5C depicts a front view of the disinfection system 700, with the front wall 719 removed to show interior features of the system. And FIG. 5D depicts a side view of the disinfection system 700, with the side wall 714 removed to show interior features of the system.

Walls 712, 714, 716, 718, 719, 736 can define a chamber 724 sized to receive objects for disinfection. While walls 712, 714, 716, 718, 719, 736 are depicted as extending substantially perpendicular from one another to define a rectangular-shaped chamber 724, it can be appreciated that disinfection systems described herein can have different configurations and/or shapes. For example, any one of walls 712, 714, 716 can extend at an off-normal axis from back wall 718, and can have a non-rectangular shape (e.g., a trapezoidal shape, a triangular shape, etc.). Walls 712, 714, 716 can define an opening 730 through which an object can be received within chamber 724.

Front wall 719 can be movable between a closed configuration (as depicted in FIG. 5A) and an open configuration (as depicted in FIG. 5B). Front wall 719 can move between the closed configuration and the open configuration, as shown via arrow B. Front wall 719 can be coupled to side wall 712 via a joint 734, and can pivot about joint 734 to move between the closed configuration and the open configuration. While front wall 719 is shown as a single panel, in other embodiments, front wall 719 can be formed of multiple panels and/or sections, and each panel can be coupled to the same or a different side wall. An example of such an arrangement is described below with reference to FIGS. 11-15. In some embodiments, front wall 719 can be coupled to side wall 712 (and/or other side walls) using a mechanical connector other than a joint, e.g., using an elastic material, a slider bar, etc. In some embodiments, disinfection system 700 can include a control unit that can electrically operate front wall 719, e.g., to move it between an open configuration and a closed configuration. Front wall 719 can be formed of a rigid and/or flexible material (e.g., metal, cloth, fabric, plastic, etc.). In some embodiments, front wall 719 can be designed to be retractable, such that it can be retracted to expose opening 730.

When front wall 719 is in the closed configuration, front wall 719 can seal opening 730 of chamber 724 such that energy (e.g., UV light) within chamber 724 does not exit chamber 724. In some embodiments, walls 712, 714, 716, 718, 719, 736 can form an air-sealed chamber such that air (e.g., air including disinfecting agent and/or neutralizing agent and/or contaminated air) cannot exit chamber 724. By sealing in energy and/or air, front wall 719 can reduce the risk of a user outside of chamber 724 from being harmed by energy and/or air present within chamber 724. When front wall 719 is in the open configuration, front wall 719 can allow access to opening 730 such that an object can be placed within chamber 724 via opening 730.

One or more of walls 712, 714, 716, 718, 719, 736 can be formed of modular units. For example, wall 712 can be formed of four modular units 712a, 712b, 712c, 712d; wall 714 can be formed of four modular units 714a, 714b, 714c, 714d; and wall 716 can be formed of four modular units 716a, 716b, 716c, 716d. In some embodiments, one or of more walls 718, 719, 736 can also be formed of modular units, including some walls being formed of a single modular unit.

Modular units 712a, 712b, 712c, 712d, 714a, 714b, 714c, 714d, 716a, 716b, 716c, 716d can be designed to be interchangeable with one another. Therefore, each modular unit can have similar components as other modular units. An inner surface of each modular unit can include at least one reflective unit 720 and at least one energy source 722. Additional reflective unit(s) 720 and/or energy source(s) 722 can be positioned on the inside surfaces of walls 718, 719, 736, as shown in FIGS. 5A-5D. For example, an inner surface of wall 718 can include at least one reflective unit 720 and, optionally, one or more energy source(s) 722. An inner surface of wall 719 can include at least one reflective unit 720 and, optionally, one or more energy source(s) 722. And an inner surface of wall 736 can include at least one reflective unit 720 and, optionally, one or more energy source(s) 722. In an embodiment, each of modular units 712a, 712b, 712c, 712d, 714a, 714b, 714c, 714d, 716a, 716b, 716c, 716d can include at least one least one reflective unit 720 and at least one energy source 722, and each of walls 718, 719, 736 can include at least one reflective unit 720. While reflective unit(s) 720 and/or energy source(s) 722 are depicted on a central portion of the modular units, it can be appreciated that reflective unit(s) 720 and/or energy source(s) 722 can be located on any portion of an inner surface of a modular unit and/or cover an entire inner surface of a modular unit. And while reflective unit(s) 720 are depicted as surrounding energy source(s) 722, it can be appreciated that reflective unit(s) 720 and/or energy source(s) 722 can be positioned in any suitable arrangement, including arrangements where reflective unit(s) 720 and energy source(s) 722 each cover an entire inner surface of a modular unit. Further examples of these and other arrangements of reflective unit(s) 720 and/or energy source(s) 722 are described below with reference to FIGS. 8A, 8B, 9A, and 9B.

Reflective unit 720 can be similar to other reflective units described herein (e.g., reflective units 120 and/or 220). For example, reflective unit 720 can include one or more reflective surfaces that can reflect energy (e.g., disinfecting light emitted by an energy source 722). In some embodiments, reflective unit 720 can be implemented as a reflective coating and/or flat reflective surface. Energy source 722 can be similar to other energy sources described herein (e.g., energy source 122 and/or 222). For example, energy source 722 can be configured to emit a light capable of disinfecting a surface of an object, such as, for example, UV light and/or HINS light. Each energy source 722 can be disposed near and/or within a reflective unit 720, such that energy emitted by the energy source 722 can be reflected and directed into chamber 724 via the reflective unit 720. Other energy sources 722 and/or reflective units 720 located on other modular units can also emit and reflect energy into chamber 724, such that a collective amount of energy sufficient for disinfection is directed into chamber 724 and/or at an object disposed within chamber 724.

In some embodiments, one or more modular units 712a, 712b, 712c, 712d, 714a, 714b, 714c, 714d, 716a, 716b, 716c, 716d, or walls 712, 714, 716, 718, 719, 736 can be movable relative to other components of disinfection system 700. For example, wall 712 and/or an individual modular unit 712a, 712b, 712c, 712d can be movable along an axis D; wall 714 and/or an individual modular unit 714a, 714b, 714c, 714d can be movable along an axis E; wall 716 and/or an individual modular unit 716a, 716b, 716c, 716d can be movable along an axis F; and wall 718 can be movable along an axis C. Additionally or alternatively, one or more reflective unit(s) 720 and/or energy source(s) 722 can be movable relative to a wall or modular unit. Movement of walls, modular units, reflective unit(s) 720, and/or energy source(s) 722 can be controlled by a control unit (e.g., a processor and/or control panel, such as processor 154 and/or control panel 150), and/or be moved manually by a user (e.g., via a mechanical mechanism, such as a lever, and/or by directly pushing or pulling on an individual component). Walls, modular units, reflective unit(s) 720, and/or energy source(s) 722 may be moved to position reflective unit(s) 720 and/or energy source(s) 722 closer to an object within chamber 724 to increase the efficiency of the disinfection process. For example, if a small object is placed within chamber 724, one or more walls, modular units, reflective unit(s) 720, and/or energy source(s) 722 may be moved to reduce the distance between the object and reflective unit(s) 720 and/or energy source(s) 722 and/or a size of the overall chamber 724, such that a greater intensity of energy is received at the surfaces of the object. Increasing the intensity of the energy received by the object can reduce disinfection time and/or improve disinfection efficacy.

While axes C, D, E, F are shown as being perpendicular to walls 718, 712, 714, 716, respectively, one of ordinary skill in the art would appreciate that walls, modular units, reflective unit(s) 720, and/or energy source(s) 722 can move in other directions, such as, for example, rotate about an axis and/or translated in angled directions.

Optionally, in some embodiments, disinfection system 700 can include a transporting element 732, such as, for example, wheels, casters, sleds, tracks, etc. Transporting element 732 may be disposed along a bottom surface of wall 736. Transporting element 732 can be similar to other transporting elements described herein (e.g., transporting element 132). For example, transporting element 732 can enable disinfection system 700 to maneuver through spaces, including rooms within a medical facility. In some embodiments, transporting element 732 can be retracted into openings formed in wall 736.

In some embodiments, wall 736 can include a ramped surface 734 to facilitate placement of an object into chamber 724 and/or removal of an object form chamber 724. In some embodiments, wall 736 can also include elements for guiding an object to a specific location within chamber 724 and/or restricting movement of the object within the chamber, such as, for example, stoppers, tracks, treads, depressions, etc. These elements can optionally be adjusted (e.g., via a processor and/or control panel, such as processor 154 and/or control panel 150) to accommodate different types of objects and/or change a placement of an object within chamber 724.

Figure 6:
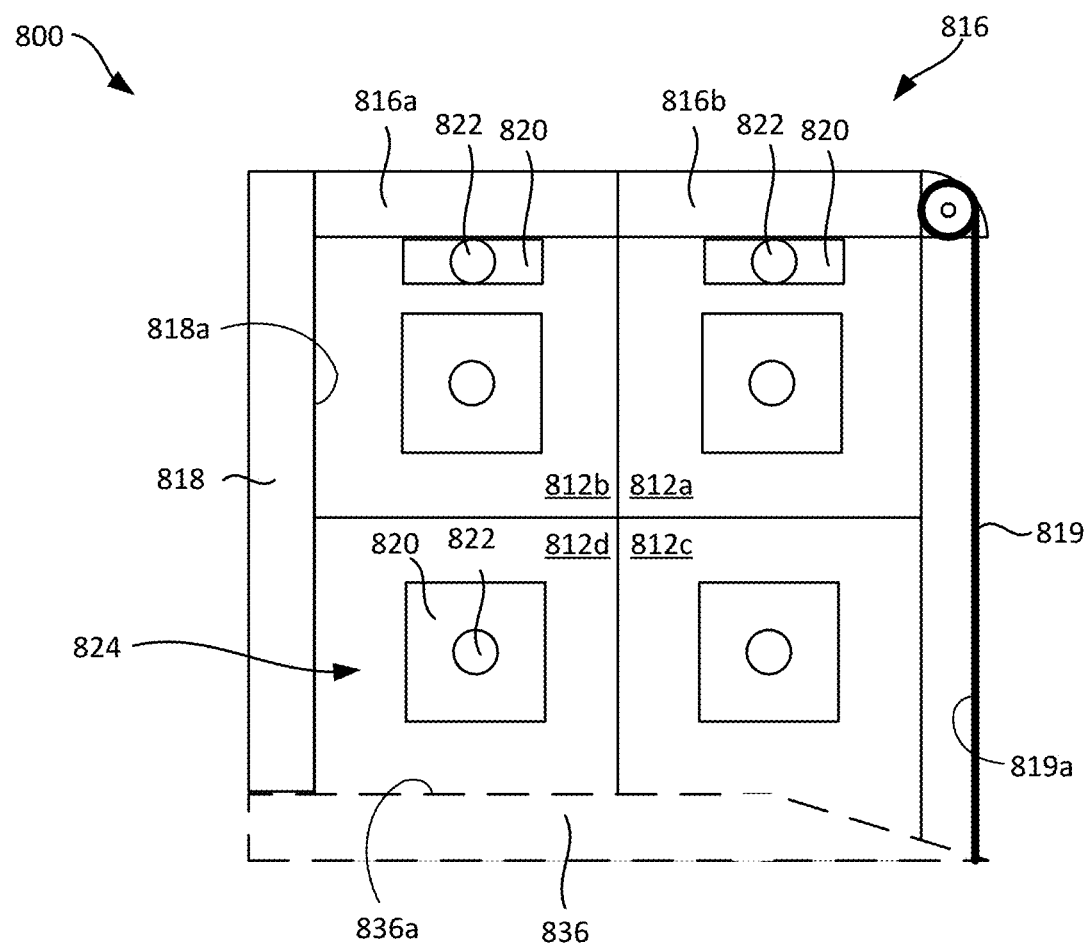
FIG. 6 schematically illustrates an example disinfection system including modular units, according to embodiments disclosed herein.

FIG. 6 schematically depicts a side view of an example disinfection system 800, according to other embodiments disclosed herein. Disinfection system 800 can include similar components as other disinfection systems described herein (e.g., disinfection systems 100, 200, and/or 700). Disinfection system 800 can include side walls (including a side wall 812), a top wall 816, a back wall 818, and optionally a bottom wall 836. In FIG. 6, a second side wall similar to wall 812 is not depicted so that an interior of disinfection system 800 can be viewed.

At least one wall of disinfection system 800 can be formed of one or more modular units. For example, side wall 812 can be formed of modular units 812a, 812b, 812c, 812d; and top wall 816 can be formed of at least two modular units 816a, 816b. Optionally, back wall 818 and/or bottom wall 836 can be formed of one or more modular units. Modular units 812a, 812b, 812c, 812d, 816a, 816b can each include at least one reflective unit 820 and at least one energy source 822. In some embodiments, back wall 818 can include a reflective inner surface 818a, and/or bottom wall 836 can include a reflective inner surface 836a. Reflective inner surfaces 818a, 836a can be implemented as a reflective coating and/or material that can reflect energy emitted by energy source(s) 822 into chamber 824. In some embodiments, inner surfaces 818a, 836a can also include an energy source configured to emit energy, such as, for example, light emitting nanoparticles. Further details regarding reflective surfaces including light emitting nanoparticles are described with reference to FIGS. 9A and 9B.

Disinfection system 800 can include a flexible curtain or drape 819 as a front wall. Curtain 819 can be configured to move between an open configuration and a closed configuration. In the closed configuration, as depicted in FIG. 6, curtain 819 can cover an opening to chamber 824. In the open configuration, curtain 819 can be retracted (e.g., rolled up) via a wheel or pulley, and/or pulled aside using another mechanical and/or electrical mechanism, to expose the opening to chamber 824 such that an object can be placed within chamber 824. Curtain 819 can include an inner surface 819a that can be a reflective surface. In some embodiments, inner surface 819a can also include at least one energy source, e.g., light emitting nanoparticles.

In some embodiments, one or more walls, modular units, reflective unit(s) 820, and/or energy source(s) 822 can be movable such that an angle or direction of reflective unit(s) 820 and/or energy source(s) 822 can be adjusted and/or a distance of reflective unit(s) 820 and/or energy source(s) 822 to an object be reduced.

Figure 7:
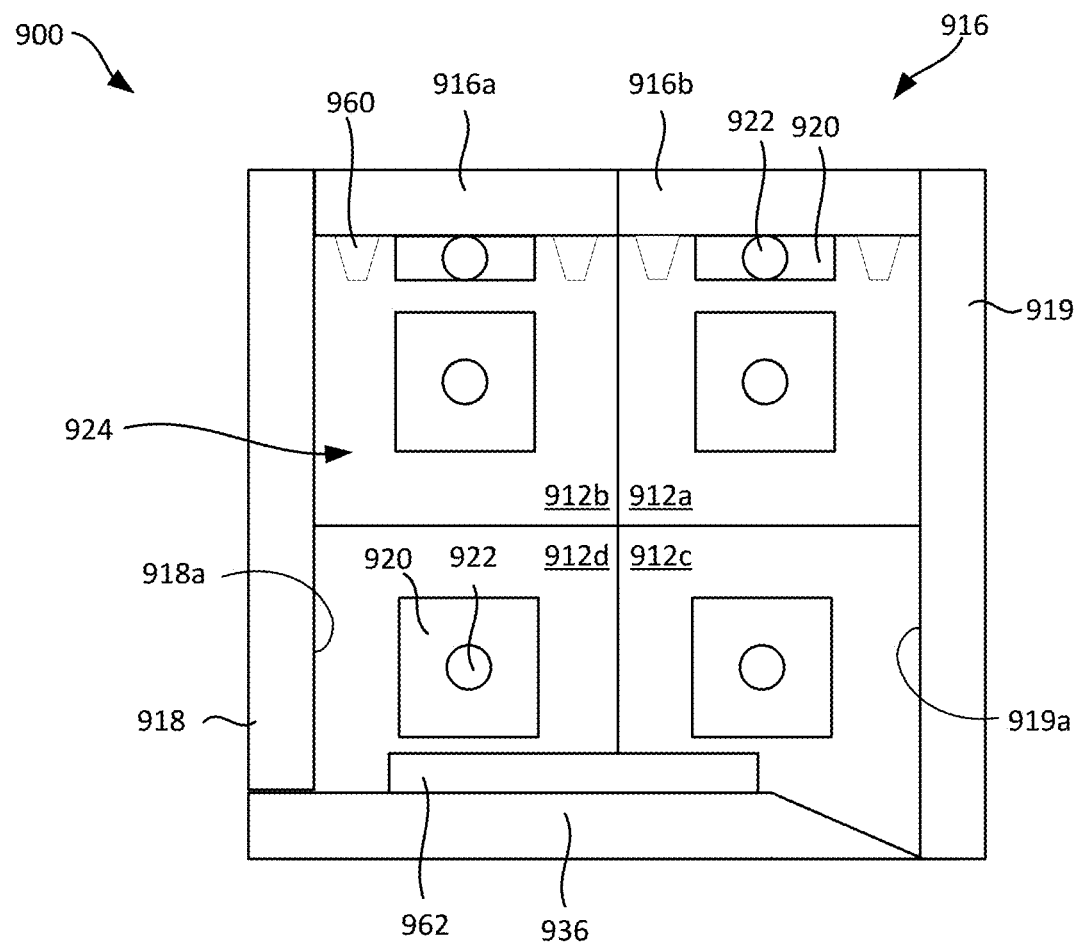
FIG. 7 schematically illustrates an example disinfection system including modular units and capable of forming a sealed chamber, according to embodiments disclosed herein.

FIG. 7 schematically depicts a side view of an example disinfection system 900, according to other embodiments disclosed herein. Disinfection system 900 can be similar to disinfection system 700 (and include components that are similar to other disinfection systems described herein), but also include at least one spray unit 960. Disinfection system 900 can include side walls (including a side wall 912), a top wall 916, a back wall 918, and a bottom wall 936. In FIG. 7, a second side wall similar to wall 912 is not depicted so that an interior of disinfection system 900 can be viewed.

At least one wall of disinfection system 900 can be formed of modular units. For example, side wall 912 of disinfection system can be formed of modular units 912a, 912b, 912c, 912d, and top wall 916 of disinfection system can be formed of at least two modular units 916a, 916b. Modular units 912a, 912b, 912c, 912d, 916a, 916b can each include at least one reflective unit 920 and at least one energy source 922. In some embodiments, one or more walls can include a reflective inner surface, e.g., back wall 918 can include a reflective inner surface 918a and/or front wall 919 can include a reflective inner surface 919a.

At least one wall and/or modular unit of disinfection chamber 900 can include a spray unit 960. For example, modular units 916a, 916b can each include spray unit(s) 960. Spray unit(s) 960 can be similar to spray unit(s) 160, as described above. For example, spray unit(s) 960 can be configured to deliver substances, including, for example, a disinfecting agent, a neutralizing agent, and/or a photosensitizer. Spray unit(s) 960 can be configured to deliver such substances as a liquid spray and/or a vapor. Spray unit(s) 960 can be located on any portion of an inner surface of a modular unit and/or wall. In some embodiments, spray unit(s) 960 can be adjusted (e.g., via a processor and/or control panel, such as processor 154 and/or control panel 150) to change a direction and/or spray profile of a sprayed substance. In some embodiments, spray unit(s) 960 can apply an electrostatic charge to the sprayed substance to encourage droplets of the substance to spread out more evenly and adhere to the neutral or negative charged surfaces of an object within chamber 924.

Walls of disinfection chamber 900 can be designed to form a fluidically sealed chamber 924 that can prevent energy and/or other substances (e.g., a disinfecting agent, a neutralizing agent, and/or a photosensitizer) from exiting chamber 924. In some embodiments, spray unit(s) 960 can be configured to deliver a single type of disinfecting agent. In other embodiments, some spray units 960 can be configured to deliver a first type of disinfecting agent while other spray units 960 can be configured to deliver a second type of disinfecting agent, e.g., in the case where different disinfecting agents may be required to kill different types of pathogens. In other embodiments, some spray units 960 can be configured to deliver a disinfecting agent while other spray units 960 can be configured to deliver a neutralizing agent, e.g., in the case where a neutralizing agent may be used to reduce the degradation effects caused by the disinfection agent. In other embodiments, some spray units 960 can be configured to deliver a disinfecting agent while other spray units 960 can be configured to deliver a photosensitizer, e.g., in the case where a photosensitizer and a disinfecting agent may be used, along with an energy source (e.g., a UV light source), to disinfect an object.

Disinfection system 900 includes at least one exhaust unit 962. Exhaust unit 962 can be similar to exhaust unit 162, described above. For example, exhaust unit 962 can be configured to circulate air into and/or out of chamber 924, including air containing a disinfecting agent and/or a neutralizing agent. Exhaust unit 962 can be disposed on an inner surface of bottom wall or base 936. Alternatively or additionally, one or more exhaust units can be disposed on other walls and/or modular units of disinfection system 900.

In some embodiments, one or more walls, modular units, reflective unit(s) 920, energy source(s) 922, and/or spray unit(s) 960 can be movable such that an angle or direction of reflective unit(s) 920, energy source(s) 922, and/or spray unit(s) 960 can be adjusted and/or a distance of reflective unit(s) 920, energy source(s) 922, and/or spray unit(s) 960 to an object be reduced.

Figure 8A:
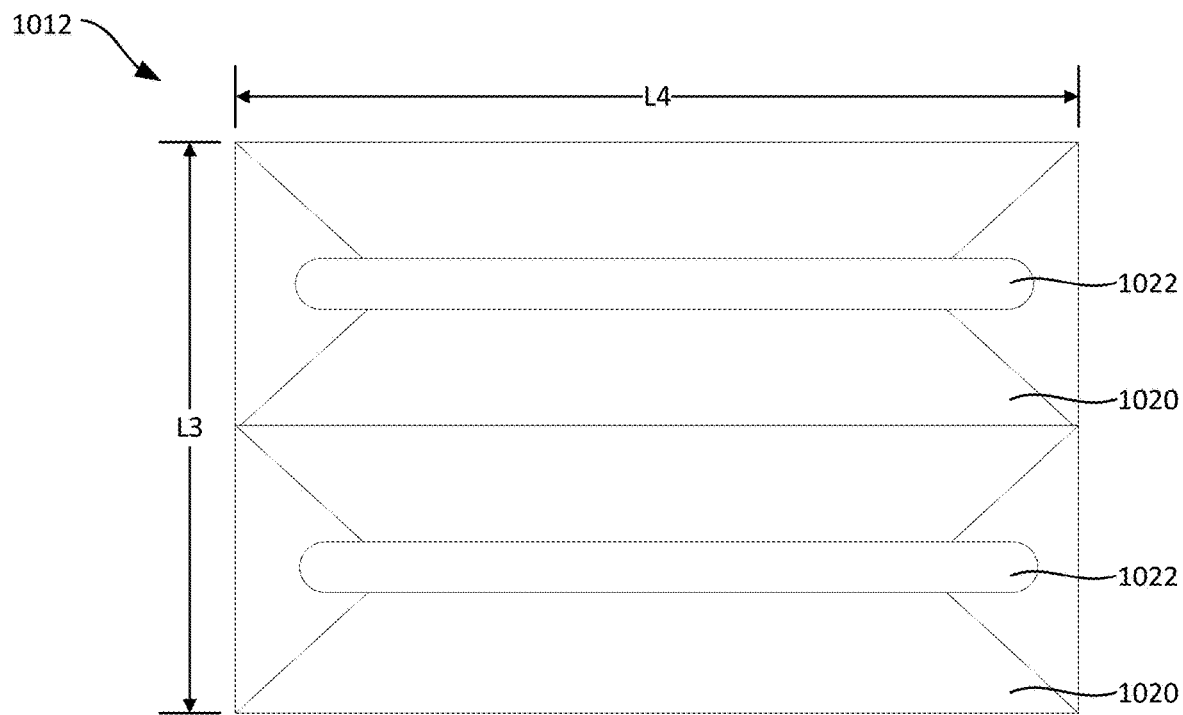
FIGS. 8A and 8B illustrate two different configurations of energy sources disposed on modular units of a disinfection system, according to embodiments disclosed herein.

FIGS. 8A, 8B, 9A, and 9B depict different configurations of modular units having one or more energy sources and/or reflective units. FIG. 8A depicts an example modular unit 1012 having two reflective units 1020 and two energy sources 1022. Modular unit 1012 can be similar to any of the modular units described herein (e.g., modular units forming a part of disinfection systems 200, 700, 800, and/or 900). Each energy source 1022 can be housed within a reflective unit 1020. Energy sources 1022 can be implemented as light bulbs or tubes, such as, for example, a mercury vapor bulb or tube, a xenon gas bulb or tube, etc. In an embodiment, each energy source 1022 can be configured to emit UV light having an intensity of at least 100 μW/cm$^2$ at 1 meter. Each reflective unit 1020 can have a concave shape such that energy emitted from each of the respective energy sources 1022 can be directed and/or focused by the reflective unit 1020 toward a disinfecting area (e.g., into a chamber) and/or an object disposed in the disinfecting area. In an embodiment, each reflective unit 1020 can have a plurality of reflective surfaces that are disposed off normal with respect to a back section of the reflective unit 1020, such that energy emitted by each of the respective energy sources 1022 can be directed in multiple directions toward a disinfecting area and/or an object disposed in the disinfecting area.

Modular unit 1012 can be shaped as a panel with a width L3 and a length L4. The width L3 and the length L4 of modular unit 1012 can be appropriately sized for treating medical equipment and/or other objects within a medical facility (e.g., a hospital). Additionally, modular unit 1012 can be dimensioned to fit through standard sized doorways and openings in medical facilities, such that the units can easily be moved between rooms. In an embodiment, modular unit 1012 can have a width L3 of approximately 25 inches and a length L4 of approximately 50 inches. Multiple modular units, such as modular unit 1012, can be stacked relative to one another to form a disinfection system having dimensions for receiving various medical equipment and/or other objects. Examples of different arrangements of modular units are described with reference to FIGS. 11-16.

Figure 8B:
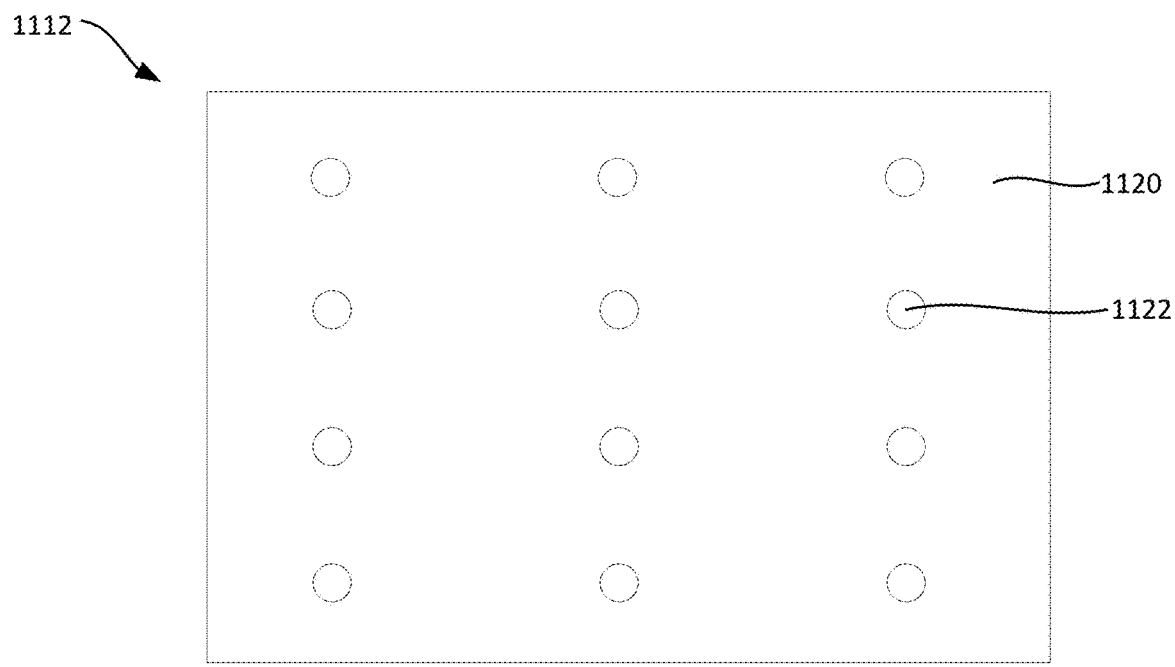

FIG. 8B depicts an example modular unit 1112 having a plurality of energy sources 1122. Energy sources 1122 can be arranged on a reflective surface 1120 acting as a reflective unit. Reflective surface 1120 can be a flat and/or curved surface that directs and/or focuses light toward a disinfecting area and/or an object located in disinfecting area. Reflective surface 1120 can be formed of a reflective material and/or include a reflective coating. Energy sources 1122 can be LEDs that are configured to emit UV and/or HINS light. Similar to modular unit 1012, modular unit 1112 can be sized to disinfect medical equipment or other objects located within a medical facility.

Figure 9A:
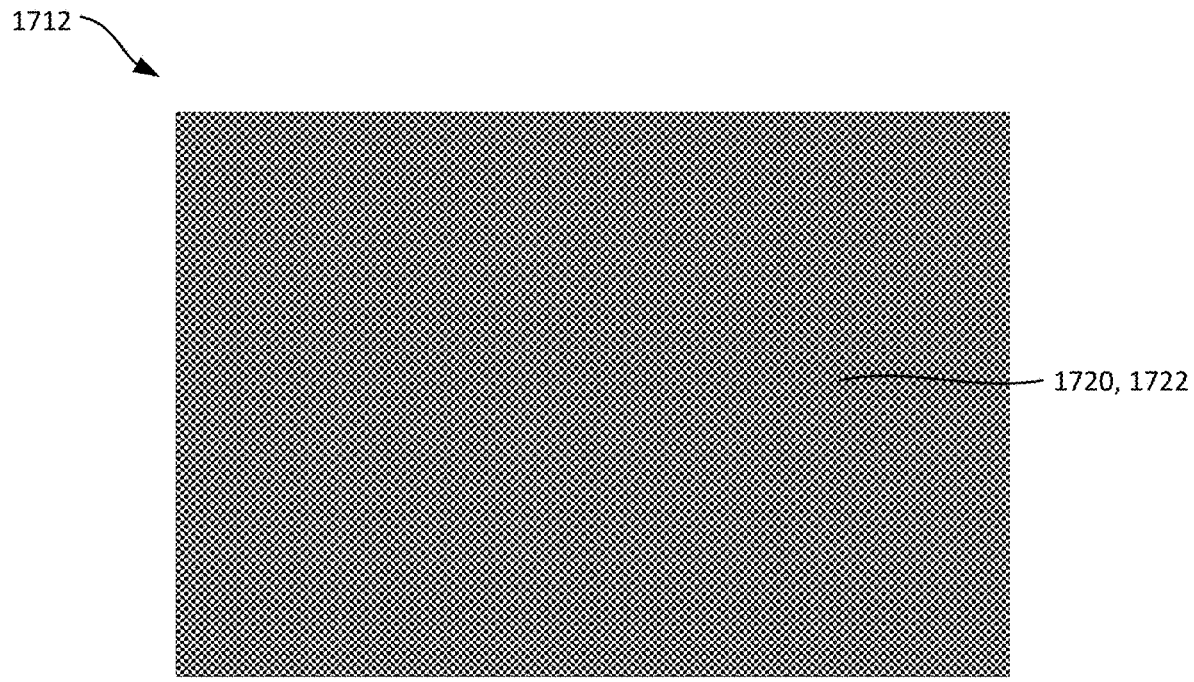
FIGS. 9A and 9B illustrate two different views of an example energy source of a disinfection system, according to embodiments disclosed herein.
Figure 9B:
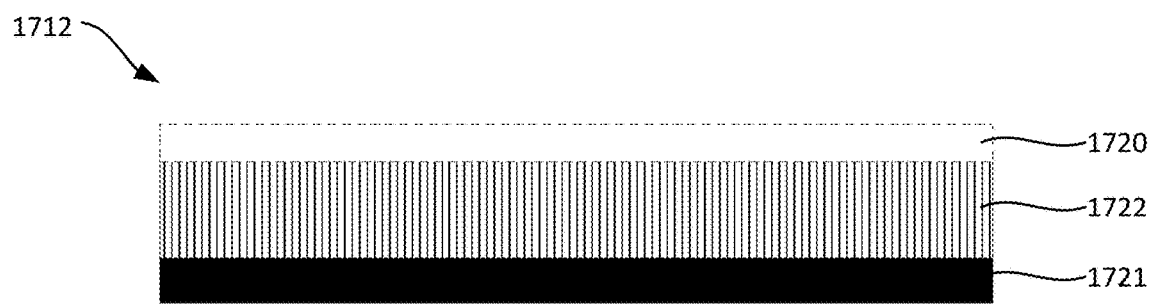

FIGS. 9A and 9B depict an example modular unit 1712 that includes a light source implemented as light emitting nanoparticles 1722. The light emitting nanoparticles 1722 can be deposited or grown on a flexible conductive layer. In an embodiment, molecular beam epitaxy (MBE) can be used to deposit nanowire heterostructures (e.g., GaN nanowires, AlGaN nanowires, InGaN nanowires) onto a conductive layer, such as, for example, a metal foil or film (e.g., a titanium foil, a tantalum foil, etc.). The nanowires may grow in arrays along the conductive layer surface. When energized (e.g., excited), the nanowires may emit energy at wavelengths between 350-400 nm. FIG. 9B provides a cross-sectional view of a portion of modular unit 1712, showing a layer of the light emitting nanoparticles 1722 deposited on a conductive layer 1721 (e.g., a metal foil or film). Suitable examples of light emitting nanoparticles are described by Sarwar et al. in "Semiconductor Nanowire Light-Emitting Diodes Grown on Metal: A Direction Toward Large-Scale Fabrication of Nanowire Devices," published Aug. 25, 2015, available at https://doi.org/10.1002/smll.201501909, and "Nanowire LEDs Grown Directly on Flexible Metal Foil," available at https://aip.scitation.org/doi/am-pdf/10.1063/1.4945419.

Optionally, a reflective layer 1720, such as a thin coat or film, can be deposited on top of the light emitting nanoparticles 1722. Reflective layer 1720 can be a partially reflective and partially transparent element. Specifically, reflective layer 1720 can be configured to allow energy emitted by light emitting nanoparticles 1722 located below reflective layer 1720 to pass through but reflect energy directed at the reflective layer 1720 in the opposite direction. Reflective layer 1720 and light emitting nanoparticles 1722 can be positioned around a disinfecting area and/or a chamber such that light emitted by nanoparticles 1722 and/or reflected by reflective layer 1720 can be directed at the disinfecting area and/or an object located in the disinfecting area. For example, when modular unit 1712 is assembled in a disinfection system having a chamber, reflective layer 1720 and light emitting nanoparticles 1722 can be located on an inside surface of the modular unit 1712 that faces the chamber such that it can direct energy into the chamber and/or at an object located in the chamber.

Similar to modular unit 1012, modular unit 1712 can be sized to disinfect medical equipment or other objects located within a medical facility.

Figure 10:
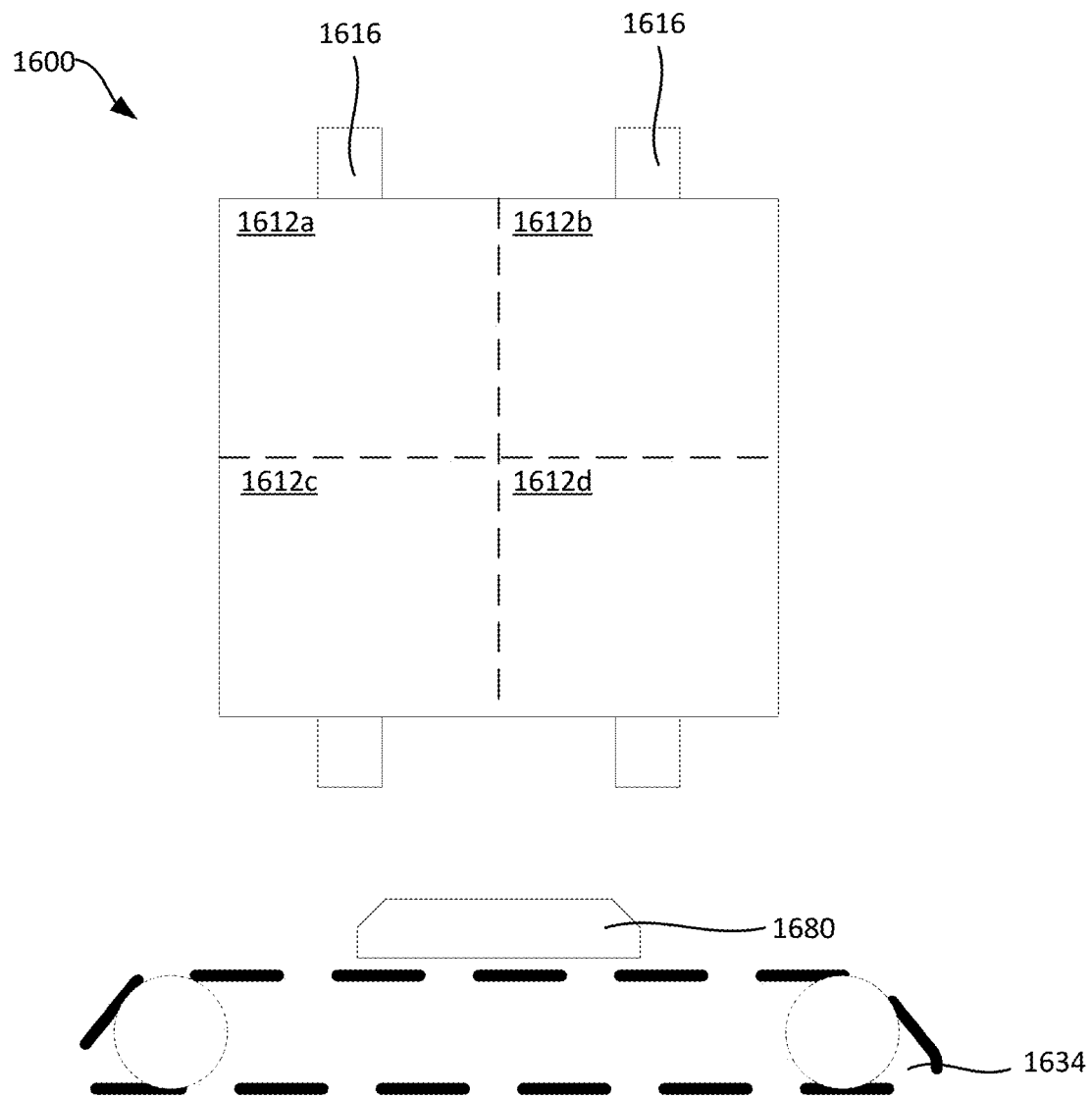
FIG. 10 schematically illustrates an example of a disinfection system, according to embodiments disclosed herein.

FIG. 10 depicts an example disinfection system 1600. Disinfection system 1600 can include similar components as other disinfection systems disclosed herein (e.g., disinfection systems 100, 200, 700, 800, and/or 900). Disinfection system 1600 can be formed of a plurality of modular units (e.g., modular units 1612a, 1612b, 1612c, 1612d), but the modular units do not form an enclosure that defines a chamber. Instead, disinfection system 1600 can be a wall-mounted or free-standing system that can focus and/or direct light at objects located in a disinfecting area (e.g., an object 1680). Modular units 1612a, 1612b, 1612c, 1612d can be supported and orientated by one or more support elements 1616 (e.g., a beam, a rod, a platform, etc.). Modular units 1612a, 1612b, 1612c, 1612d can be similar to other modular units described herein (e.g., modular unit 212a), and can include components such as a connector, an energy source, a reflective unit, a spray unit, an exhaust unit, and/or a sensor.

Disinfecting area can be, for example, a section of a room that is closed off using curtains or other barriers. Objects, such as object 1680, can be transported into the disinfecting area via a transport device 1634, such as, for example, a moving track. Alternatively, objects can be placed in disinfecting area by a user and/or a mechanical and/or electrical device (e.g., a robotic device).

Disinfection system 1600 can have a processor and/or control panel (not depicted) configured to control the operation of disinfection system 1600. Optionally, disinfection system 1600 can also have other components, e.g., a source of disinfecting agent, neutralizing agent, etc., and/or a transporting element, such as described with reference to disinfection system 100 depicted in FIG. 1.

Figure 11:
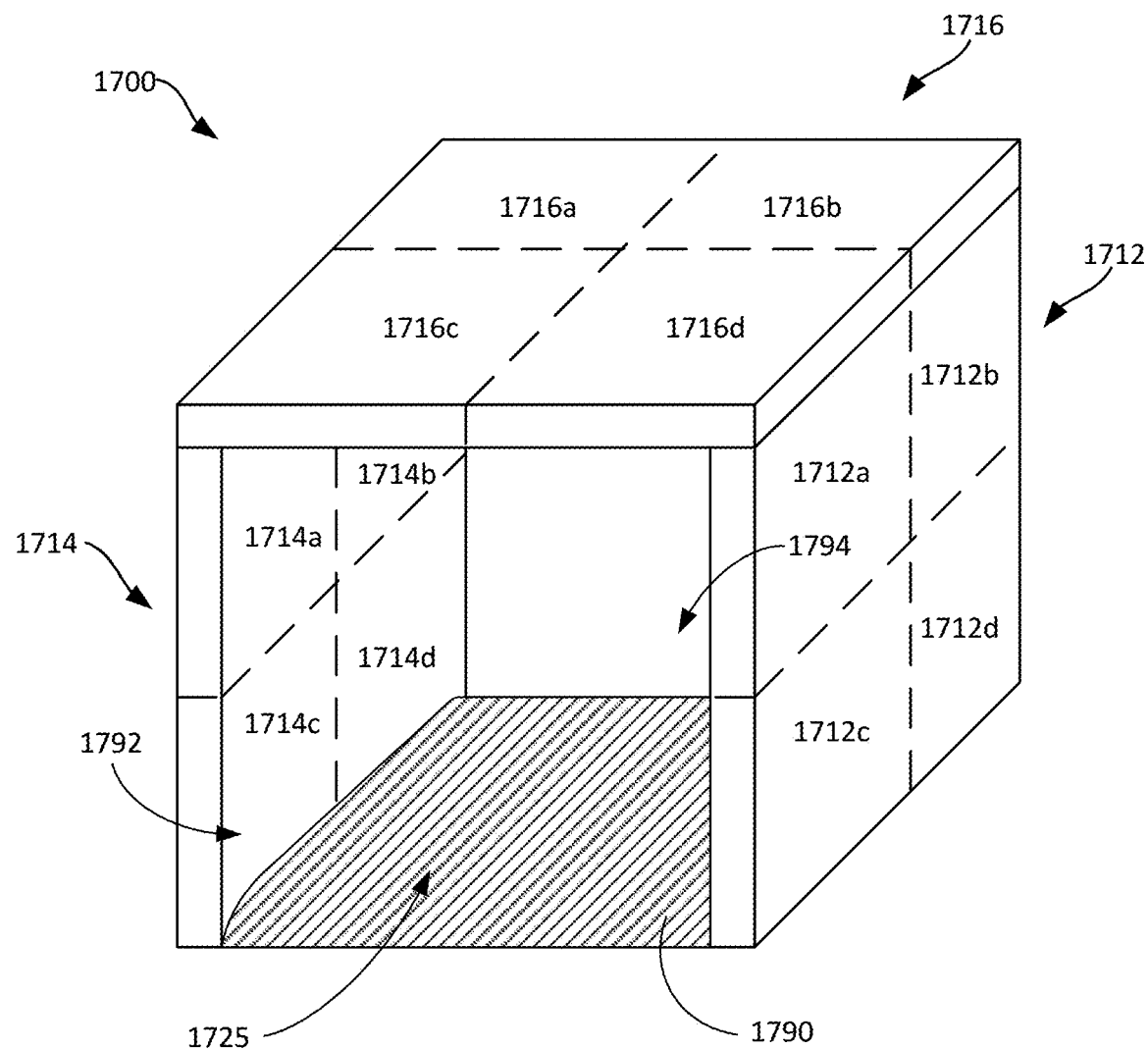
FIG. 11 schematically illustrates an example of a disinfection system, according to embodiments disclosed herein.

FIG. 11 depicts an example disinfection system 1700. Disinfection system 1700 can include similar components as other disinfection systems disclosed herein (e.g., disinfection systems 100, 200, 700, 800, 900, and/or 1600), and additionally include or be designed for use with a transport unit 1790. Disinfection system 1700 can be formed of one or more modular units. For example, disinfection system 1700 can include side walls 1712, 1714 and a top wall 1716 that can be optionally formed of one or more modular units. For example, wall 1712 can optionally be formed of four modular units 1712a, 1712b, 1712c, 1712d; wall 1714 can optionally be formed of four modular units 1714a, 1714b, 1714c, 1714d; and wall 1716 can be formed of four modular units 1716a, 1716b, 1716c, 1716d. Alternatively, each of walls 1712, 1714, 1716 can be formed of a single modular unit, two modular units, or any other number of modular units. One or more modular units 1712a, 1712b, 1712c, 1712d, 1714a, 1714b, 1714c, 1714d, 1716a, 1716b, 1716c, 1716d can be similar to other modular units, e.g., include the same components (e.g., energy source(s), reflective unit(s), spray unit(s), etc.).

Each modular unit can be manufactured and/or assembled at a manufacturing facility and transported to a location for onsite assembly into disinfection system 1700. Each modular unit can be coupled to the modular units adjacent to it via suitable fastening elements (e.g., mechanical fasteners, magnets, adhesives, etc.). In some embodiments, modular units can include built-in connectors for quick coupling and assembly, e.g., snap-on connectors, magnetic connectors, etc.

As depicted in FIG. 11, disinfection system 1700 does not include a front wall or a back wall. Rather, side walls 1712, 1714 and top wall 1716 define an open disinfecting area 1725. Disinfection system 1700 can include a transport device 1790 that transport objects through the disinfecting area 1725. For example, objects can be placed on the transport device 1790 on a first side of the disinfection system 1700 and be transported through a first opening 1792 on the first side into the disinfecting area 1725, and out through a second opening 1794 on a second side of the disinfection system 1700. While the object is being transported through the disinfecting area 1725, the object can be disinfected by one or more energy source(s), reflective unit(s), and/or spray unit(s) located on the modular units of the disinfection system 1700.

The transport device 1790 can be any suitable device for moving an object through an area. For example, the transport device 1790 can be a conveyor belt that extends along a bottom side of the disinfection unit 1790. Alternatively or additionally, the transport device 1790 can include robotic components (e.g., robotic arms, manipulators, etc.) configured to couple to the objects (e.g., grab, magnetically couple, etc.) and move them through the disinfecting area 1725 (e.g., by lifting, pulling, etc.). In some embodiments, the transport device 1790 can be designed to re-position an object (e.g., using tracks, flippers, manipulators, etc.) prior to or during movement of the object through the disinfecting area 1725.

Since the disinfecting area 1725 is not entirely sealed from the surrounding environment, disinfection system 1700 can be designed for use with energy sources and/or disinfecting agents that are not harmful to surrounding objects and/or persons. For example, disinfection system 1700 can include light sources that are excimer lamps that emit far UV-C light, e.g., light having a wavelength of approximately 222 nm.

FIGS. 12-16 illustrate different views of an example disinfection system 1200. Disinfection system 1200 can be similar to other disinfection systems described herein (e.g., disinfection systems 100, 200, 700, 800, and/or 900), and can include similar components as those systems. Disinfection system 1200 includes a plurality of walls, including side walls 1212, 1214, a top wall 1216, and a back wall 1218. Each wall 1212, 1214, 1216, 1218 can be formed from two modular units. Specifically wall 1212 is formed of modular units 1212a, 1212b; wall 1214 is formed of modular units 1214a, 1214b; wall 1216 is formed of modular units 1216a, 1216b; and wall 1218 is formed of modular units 1218a, 1218b.

Figure 12:
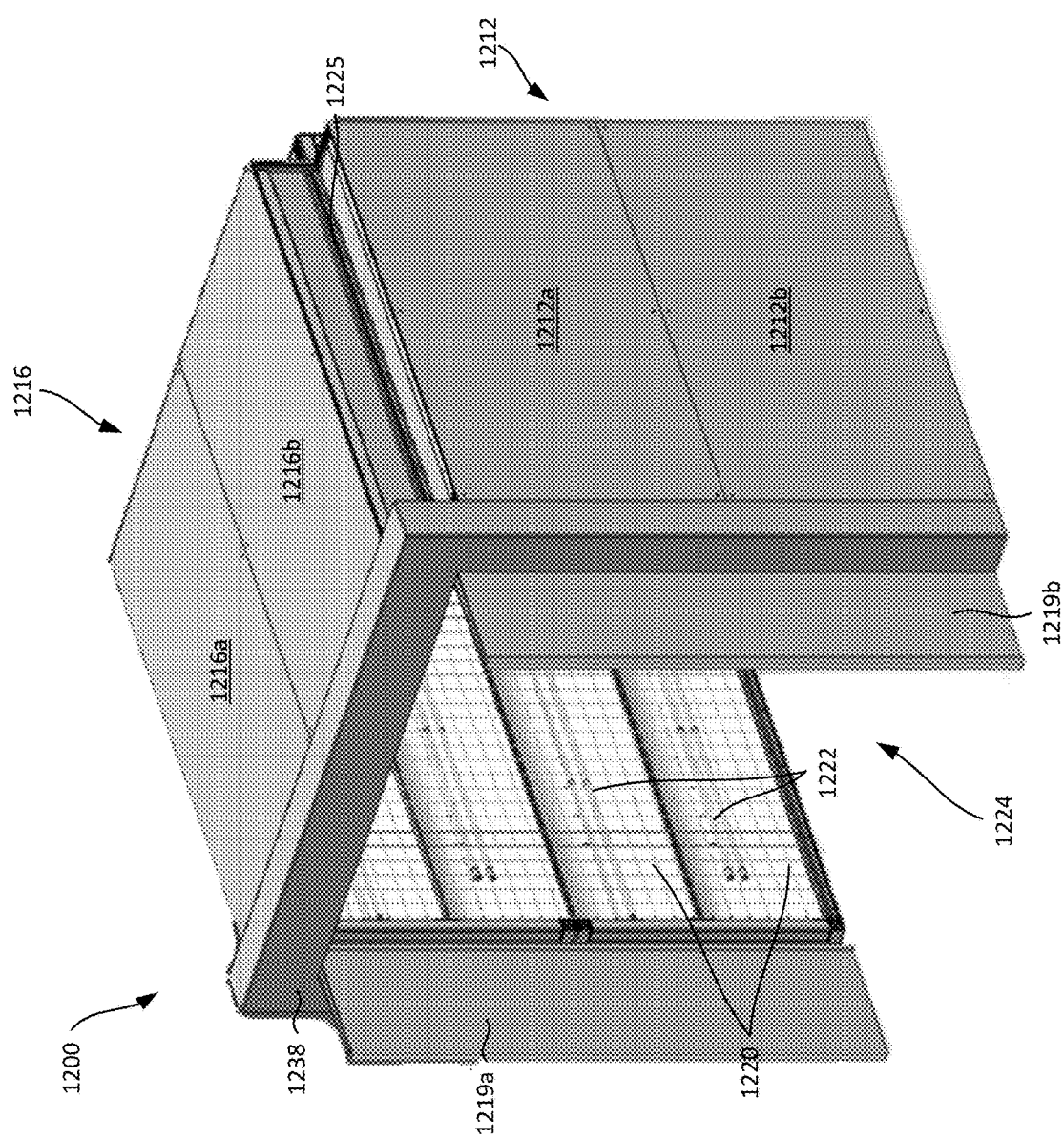
FIG. 12 is a perspective view of an example of a disinfection system including modular units, according to embodiments disclosed herein.
Figure 16:
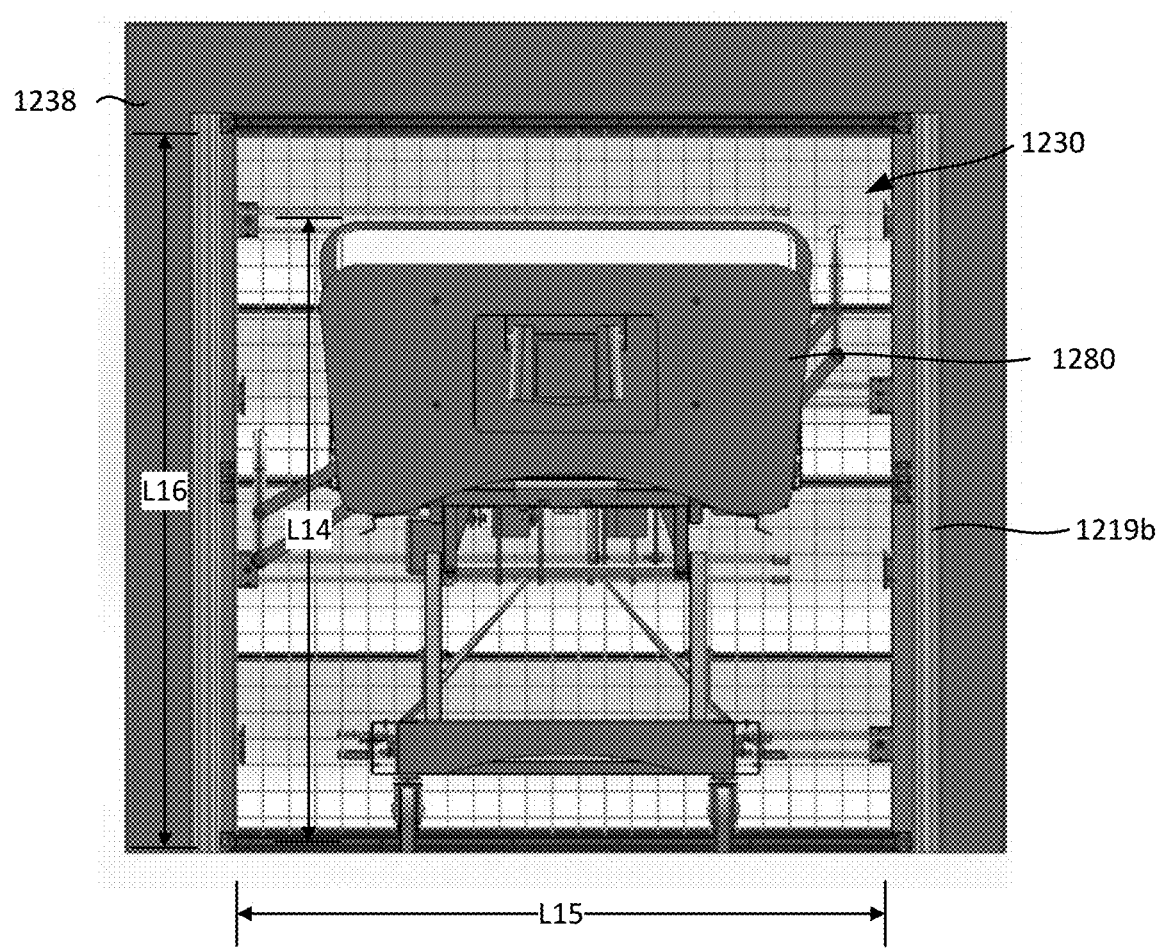
FIG. 16 depicts a front view of the disinfection system shown in FIG. 11, including an example of medical equipment disposed within the disinfection system.

Disinfection system 1200 also includes two panel sections 1219a, 1219b that can open and close. Panel sections 1219a, 1219b can be two bi-folding doors. When panel sections 1219a, 1219b are in an open configuration, as best shown in FIGS. 12 and 16, panel sections 1219a, 1219b provide an opening 1230 into a chamber 1224 defined by walls 1212, 1214, 1216, 1218. When panel sections 1219a, 1219b are in a closed configuration, panel sections 1219a, 1219b seal off opening 1230 such that energy and/or fluids (e.g., air, liquid, vapor) within chamber 1224 cannot exit chamber 1224. Each panel section 1219a, 1219b can fold into its open configuration (as shown in FIGS. 12 and 16) and unfold into its closed configuration. Panel sections 1219a, 1219b can be mounted to a support frame 1238, which can be coupled to modular units 1212a, 1212b, 1214a, 1214b, 1216a, 1216b. When panel sections 1219a, 1219b are in the open configuration, opening 1230 has a length L15 and a height L16, as shown in FIG. 16. While two panel sections 1219a, 1219b are shown, one of ordinary skill in the art would appreciate that other suitable components for closing and opening a chamber opening can be used, such as, for example, a single door that can pivot open and close, a single bi-folding door that can fold and unfold to open and close, a pair of doors that can pivot open and close, a retractable curtain, etc.

Each modular unit 1212a, 1212b, 1214a, 1214b, 1216a, 1216b, 1218a, 1218b can be connected to adjacent modular units via one or more connectors 1225. Connectors 1225 can be attachable to and/or integrated into one or more modular units. For example, connectors 1225 can include snap-on components that can mate with one another to connect two modular units together. Alternatively or additionally, connectors 1225 can include fasteners, adhesives, magnets, etc. that can adhere two adjacent modular units to one another. In some embodiments, connectors 1225 can include electrical connections and/or fluid connections, which can connect to electrical connections and/or fluid connections in adjacent modular units such that a network of electrical connections and/or fluid connections can be formed to connect one or more components of modular units 1212a, 1212b, 1214a, 1214b, 1216a, 1216b, 1218a, 1218b to power source(s), fluid source(s), a control panel, a processor, and/or other centralized elements.

FIGS. 13A, 13B, 14A, and 14B provide detailed views of modular units 1212a, 1212b of wall 1212. While not depicted in detail, other modular units of disinfection system 1200 (e.g., modular units 1214a, 1214b, 1216a, 1216b, 1218a, 1218b) can be identical to and/or similar to modular units 121a, 1212b. Each modular unit 1212a, 1212b includes two reflective units 1220 and two energy sources 1222. Reflective units 1220 and/or energy sources 1222 can be similar to other reflective units and energy sources described herein. For example, each reflective unit 1220 can have a reflective surface that can reflect energy emitted by energy sources 1222 into chamber 1224. As depicted in FIGS. 13A, 13B, 14A, and 14B, each reflective unit 1220 can have a hyperbolically shaped reflective surface that can be configured to distribute energy emitted by energy sources 1222 and reflect it into chamber 1224. Each energy source 1222 can be disposed within a reflective unit 1220. Energy sources 1222 can include at least one light tube configured to emit disinfecting light (e.g., UV light). Energy sources 1222 can be connected to electrical connectors 1226 disposed within or adjacent to each reflective unit 1220.

In some embodiments, additional reflective units 1220 and/or energy sources 1222 can be disposed on an inner surface of a front wall (e.g., panels 1219a, 1219b) and a bottom side of chamber 1214. For example, reflective material (e.g., a coating and/or flat sheet) can be placed on panels 1219a, 1219b and/or a floor of chamber 1224 and function as reflective units 1220. Reflective units 1220 and energy source 1222, when assembled around chamber 1224 and operating together, can be configured to collectively deliver a sufficient amount of light at a sufficient intensity onto the surfaces of an object within chamber 1224, such that the object can be adequately disinfected.

Figure 13B:
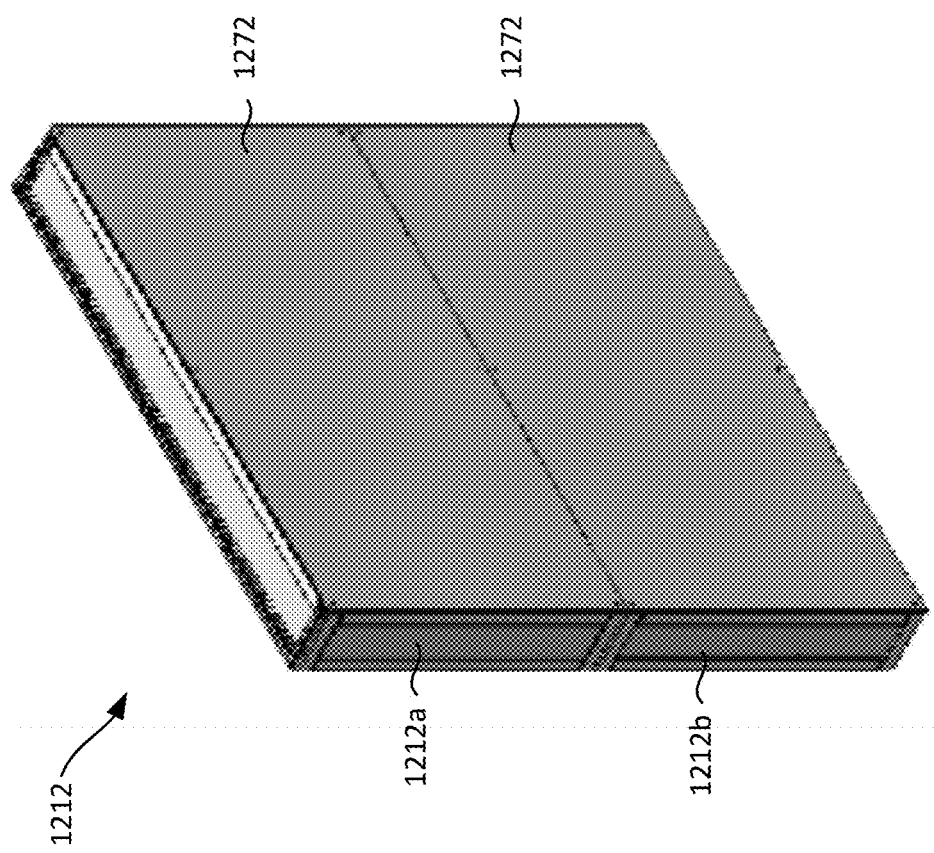
FIGS. 13A and 13B depict different views of a modular unit of the disinfection system shown in FIG. 11.
Figure 13A:
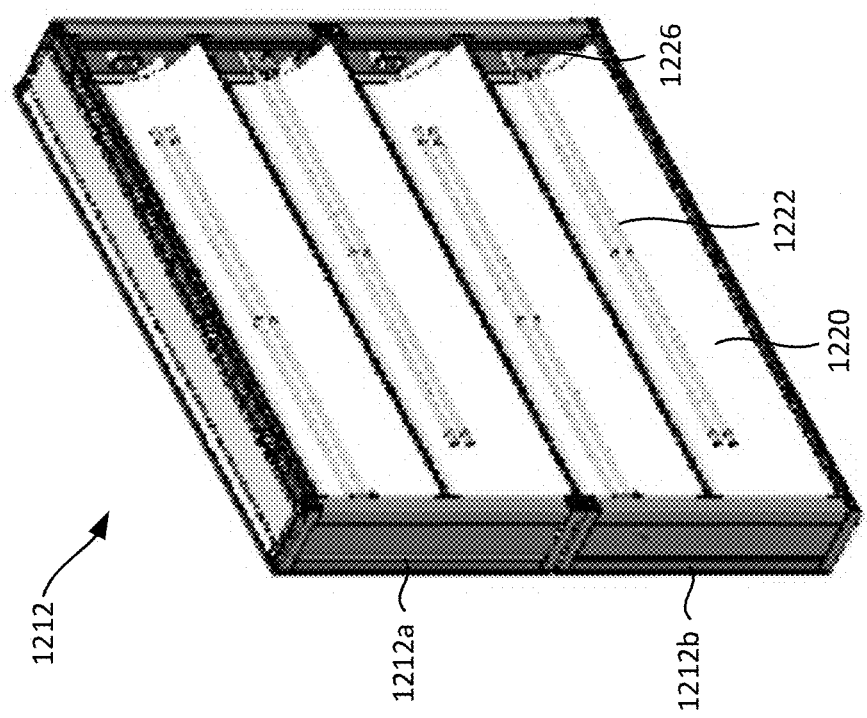
Figure 14A:
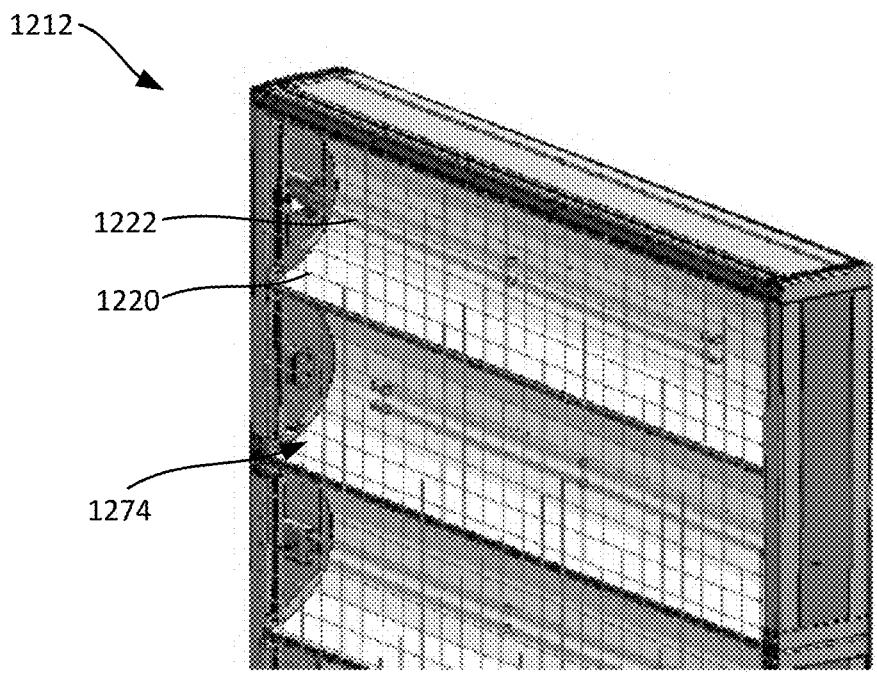
FIG. 14A depicts an enlarged view of a portion of a modular unit of the disinfection system shown in FIG. 11.
Figure 14B:
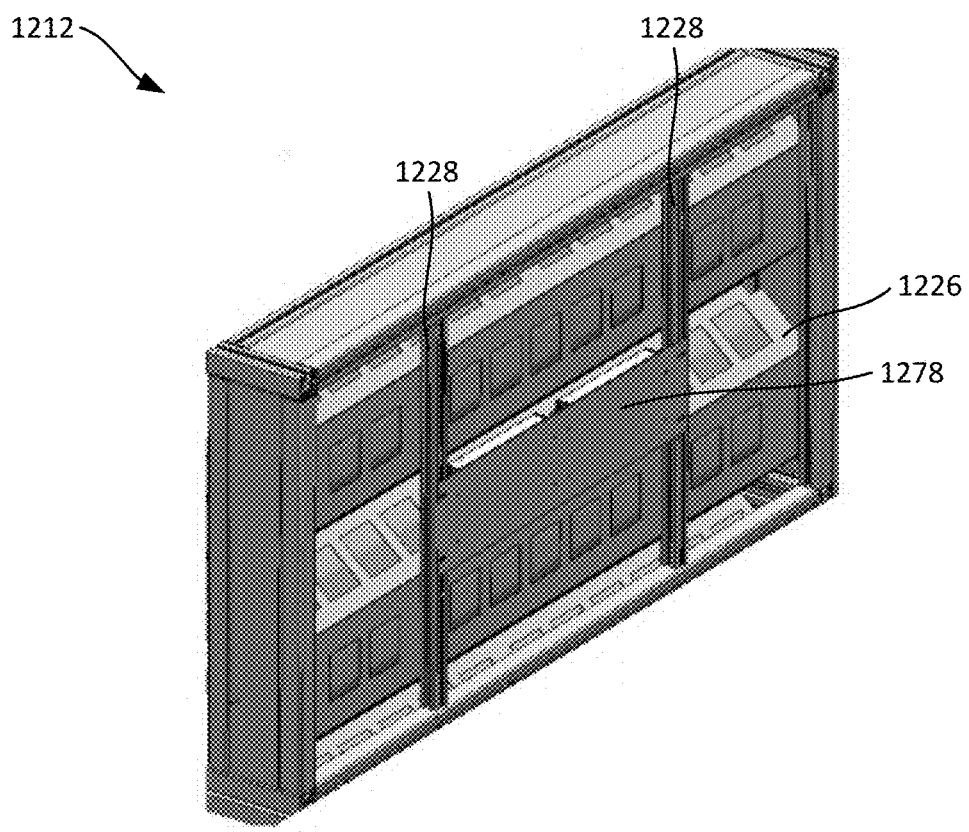
FIG. 14B depicts an enlarged view of a portion of a modular unit of the disinfection system shown in FIG. 11, with a portion of an outer housing of the modular unit removed to shown an interior support structure of the modular unit.

Each modular unit includes at least one removable cover or panel (e.g., panels 1272, 1274) to allow reflective units 1220 and/or energy sources 1222 to be inspected, repaired, or replaced. For example, FIG. 13A provides a view of modular units 1212a, 1212b with panels 1274 removed, and FIG. 14B provides a view of a portion of modular unit 1212a with panel 1272 removed. Removal of any one of panels 1272, 1274 can expose an internal structure of the modular unit and provide access to reflective units 1220 and/or energy sources 1222. The internal support structure can include one or more vertical support elements 1228 and/or horizontal support elements 1278. A back portion 1226 of reflective units can be mounted to one or more support elements 1228, 1278. In some embodiments, additional components (e.g., energy sources, spray units, etc.) can also be mounted directly to a support element. Panels 1272, 1274 can be configured to protect reflective units 1220 and/or energy sources 1222, as well as other internal components of the modular units.

In some embodiments, each modular unit can be easily detached from its adjacent modular units and removed from the disinfection system 1200 for inspection, repair, and/or replacement. In some embodiments, removal of a single modular unit does not compromise the overall structure of disinfection system 1200, such that a single modular unit can be removed while the remaining, assembled modular units remain in place, e.g., supported by one another and/or surrounding support structure (e.g., support frame 1238). Placement of a new modular unit (or the old modular unit after undergoing inspection and/or repair) can then be efficiently accomplished without requiring significant reassembly efforts.

Figure 15A:
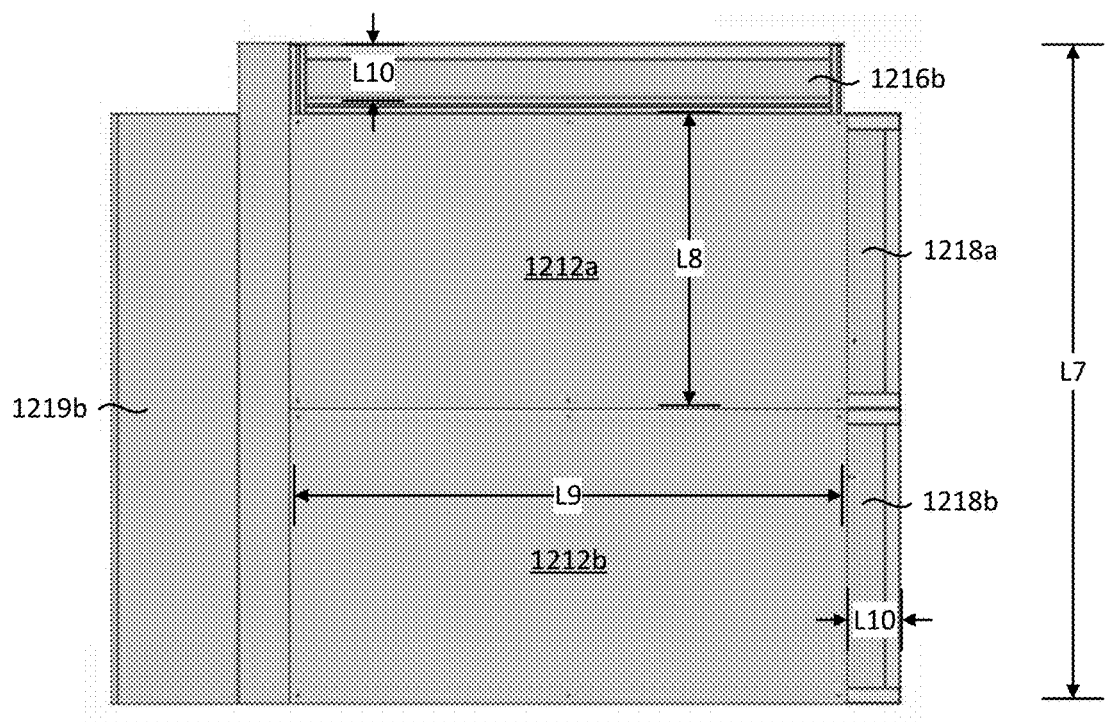
FIGS. 15A and 15B depict different views of the disinfection system shown in FIG. 11.
Figure 15B:
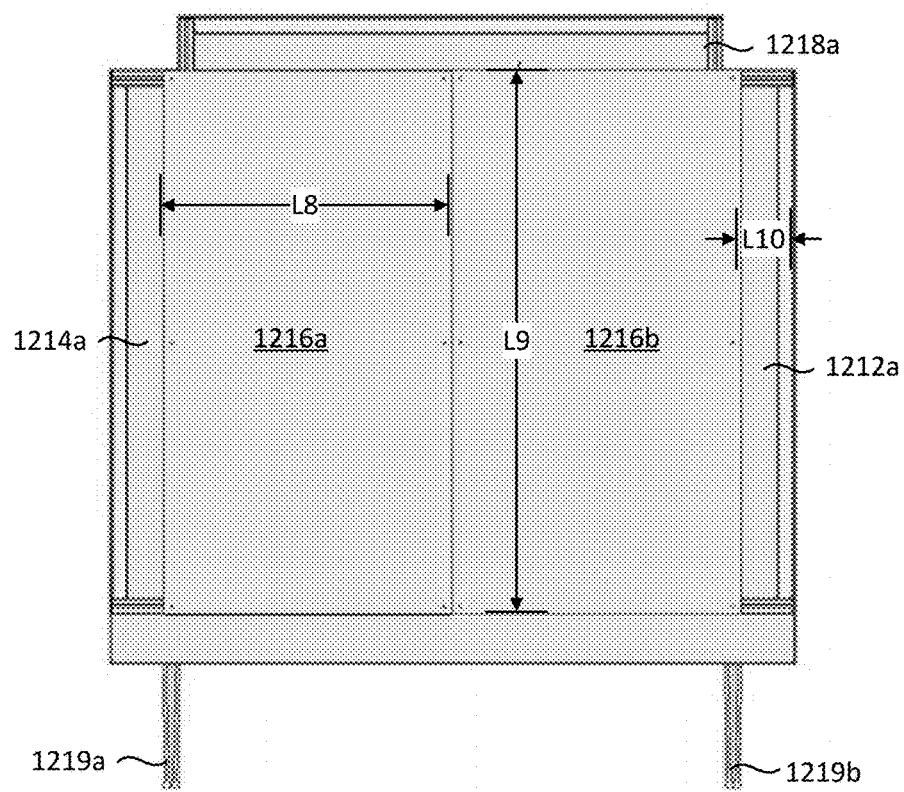

FIG. 15A depicts a side view of disinfection system 1200, and FIG. 15B depicts a top view of disinfection system 1200. As identified in FIGS. 15A and 15B, each modular unit 1212a, 1212b, 1214a, 1214b, 1216a, 1216b, 1218a, 1218b can have a width L8, a length L9, and a thickness L10. Two modular units can be stacked, one on top of the other, to form each of side walls 1212, 1214 and back wall 1218, and two modular units placed side-by-side can form top wall 1216. Accordingly, the length L9 of the modular units can be equal to two times the width L8 of the modular units.

According to some embodiments, disinfection system 1200 can be sized to receive medical equipment 1280, such as wheelchairs, IV poles, medical carts, mobile or portable computer stations, dialysis machines, anesthesia machines, ECG machines, and/or other types of mobile medical equipment. To form a chamber 1224 and an opening 1230 that are sized to receive standard-sized wheelchairs, portable computer stations, and/or medical carts, modular units having a width L8 of approximately 25 inches and a length L9 of approximately 50 inches can be used. Two modular units can be stacked on each of three sides of disinfection system 1200 (i.e., walls 1212, 1214 and back wall 1218) and two modular units can be used for top wall 1216, such that a 50-by-50-by-50-inch enclosure can be formed.

Figure 17:
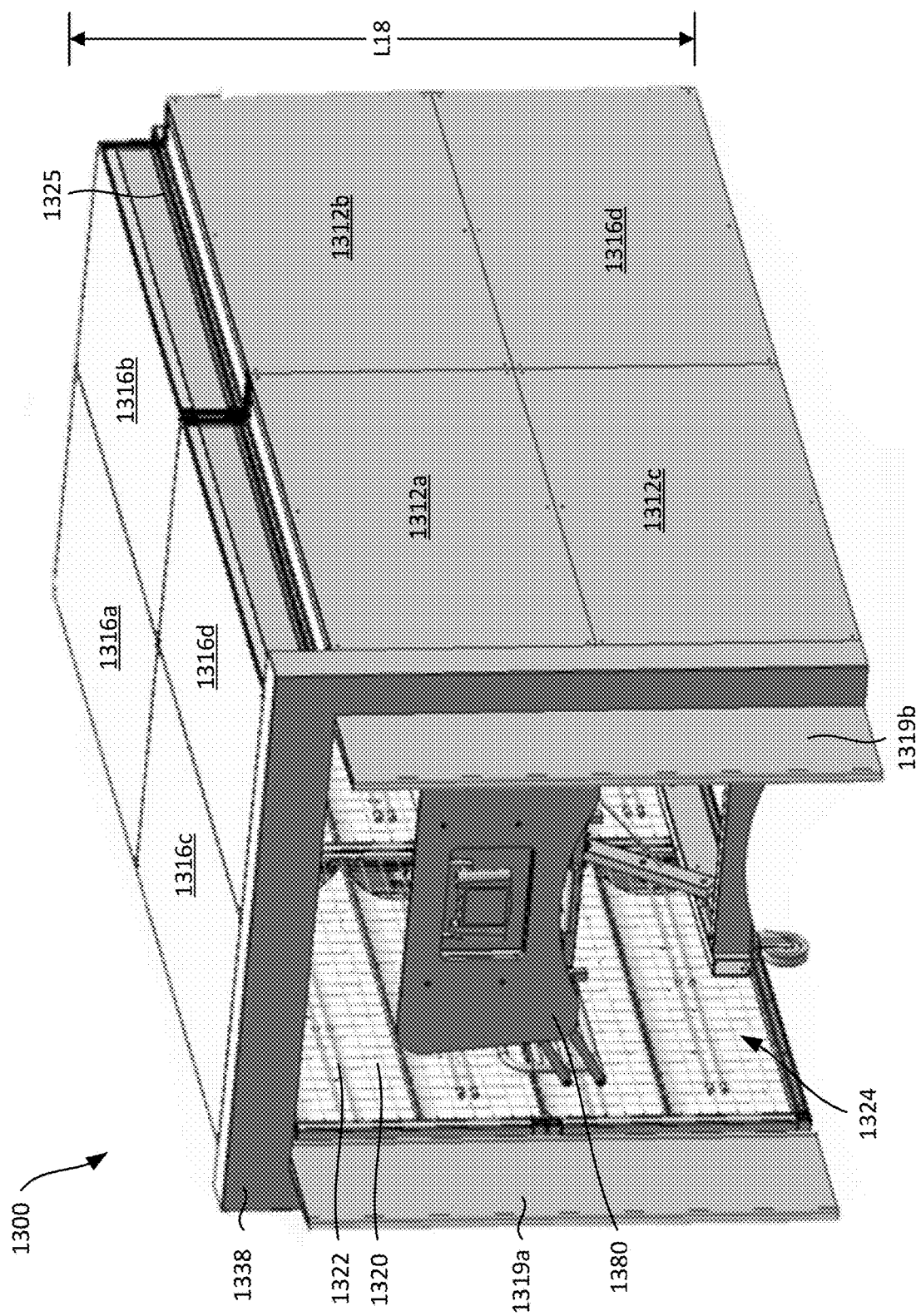
FIG. 17 depicts a perspective view of an example of a disinfection system including modular units, according to embodiments disclosed herein.

Alternatively, modular units having a width L8 of approximately 25 inches and a length L9 of approximately 50 inches can be arranged two-by-two to form two side walls, two high to form a back wall, and two-by-two to form a top wall, such that a 50-by-100-by-50-inch enclosure can be formed. Examples of medical equipment that can be received in such an enclosure can include standard-sized gurneys, wheelchairs, portable computer stations, and/or medical carts. FIG. 17 depicts an example disinfection system 1300 having such an arrangement. As depicted, each of walls 1312, 1314 can be formed of four modular units (i.e., wall 1312 can be formed of modular units 1312a, 1312b, 1312c, 1312d, and wall 1314 can be formed of modular units 1314a, 1314b, 1314c, 1314d), back wall (not depicted) can be formed of two modular units, and a top wall 1316 can be formed of four modular units 1316a, 1316b, 1316c, 1316d. Disinfection system 1300 can be similar to disinfection system 1200, except for the different arrangement of modular units. Accordingly, disinfection system 1300 can have panel sections 1319a, 1319b, a chamber 1324, reflective units 1320, energy sources 1322, connectors 1325, and a support frame 1338, similar to those of disinfection system 1200. As depicted, disinfection system 1300 can be sized to receive a piece of medical equipment, such as a gurney 1380, within its chamber 1324.

Panel sections 1319a, 1319b can function as a door of disinfection system 1300. Panel sections 1319a, 1319b can each be bi-folding doors that fold to expose an opening to chamber 1324 and unfold to close the opening. While two panel sections or bi-folding doors are shown in FIG. 17, it can be appreciated that a single larger bi-folding door that is attached to one side of support frame 1338 can be used in the alternative.

Alternatively, modular units having a width L8 of approximately 25 inches and a length L9 of approximately 50 inches can be arranged three high to form three sides (i.e., two side walls and a back wall) and two long to form a top wall, such that a 50-by-50-by-75-inch enclosure can be formed. Examples of medical equipment that can be received in such an enclosure can include standard-sized wheelchairs, wheelchairs with attached IV poles, IV poles, portable computer stations, medical carts, dialysis machines, and/or anesthesia machines.

Figure 18:
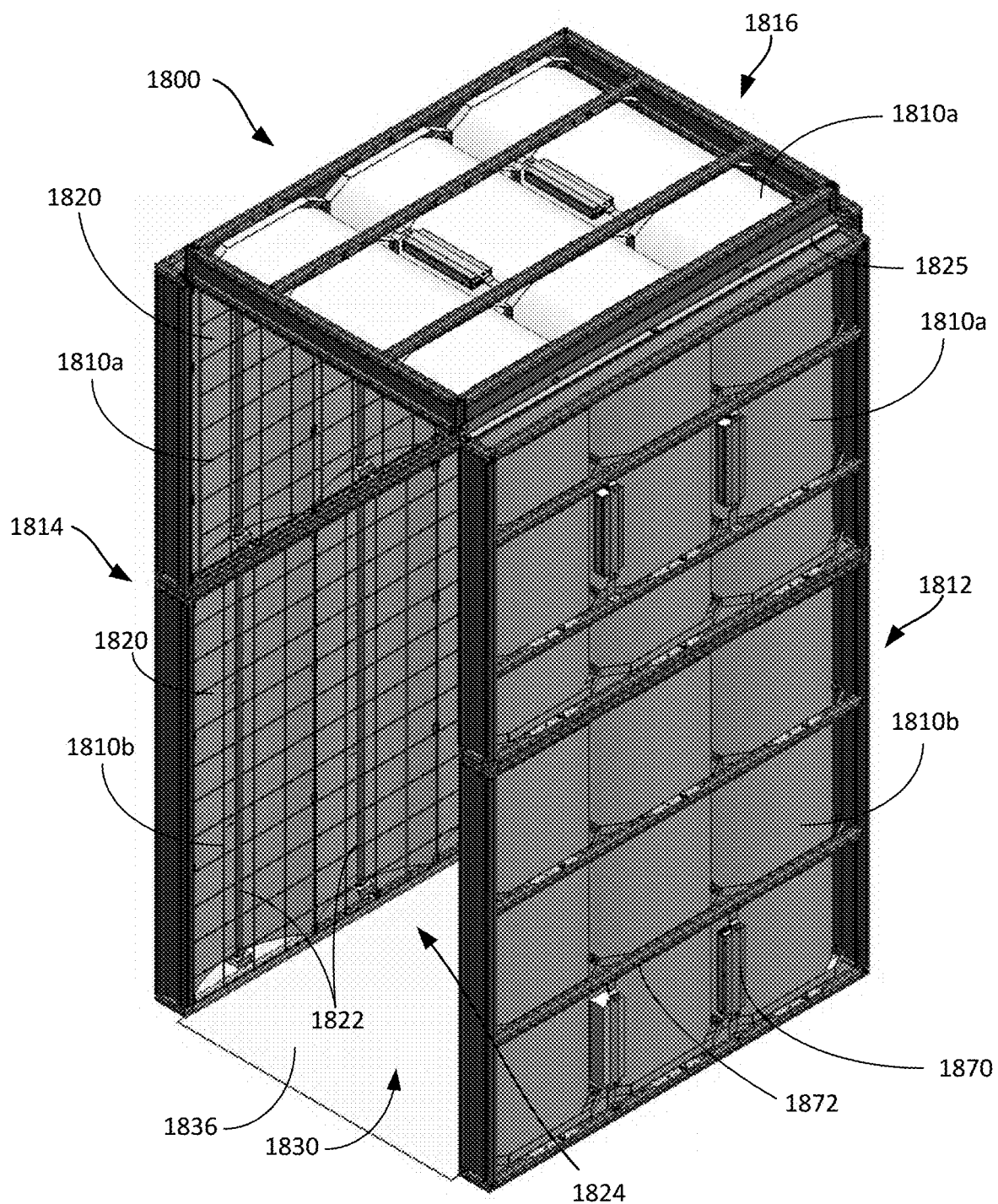
FIG. 18 is a perspective view of an example of a disinfection system including modular units, according to embodiments disclosed herein.
Figure 19:
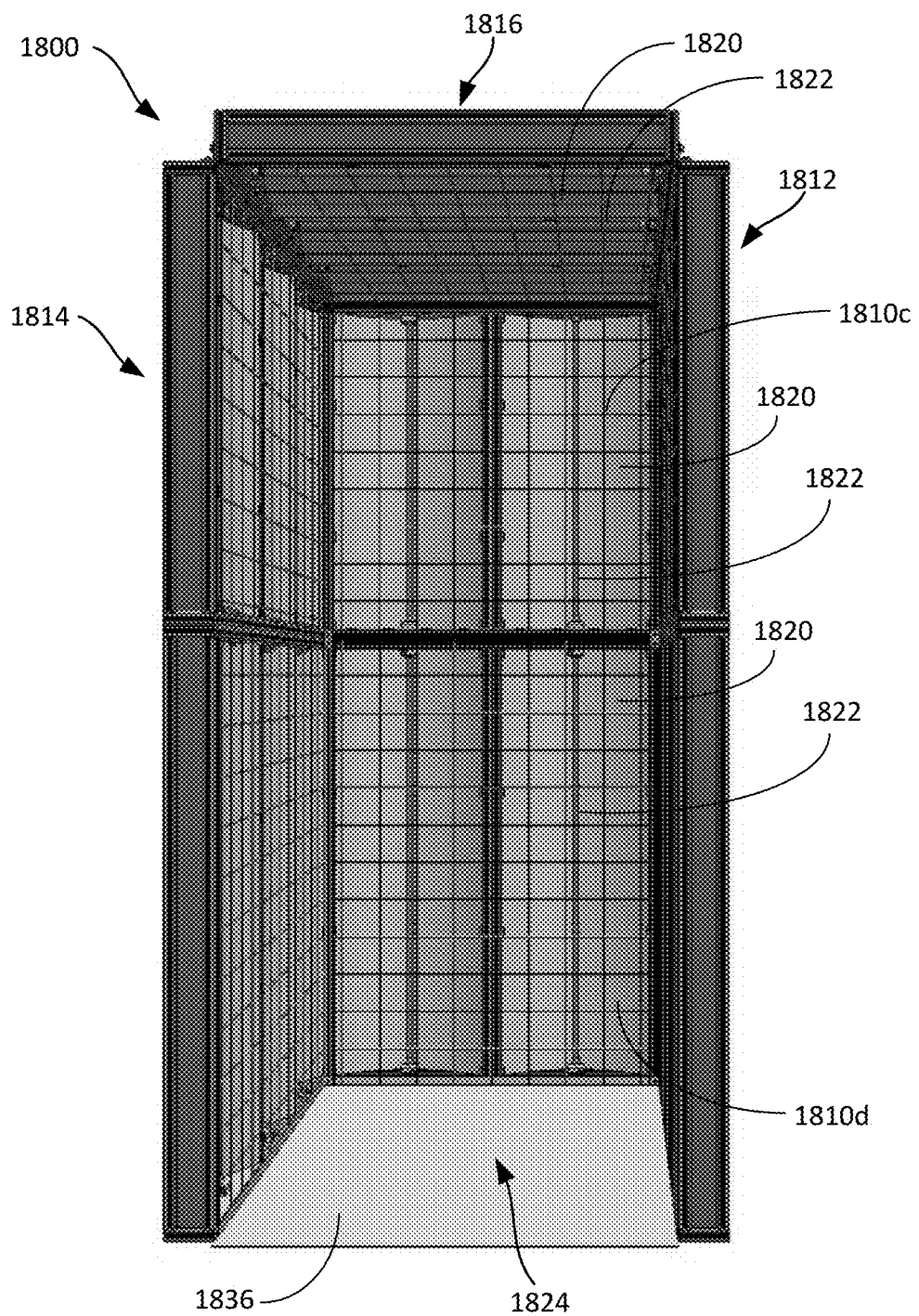
FIG. 19 is a front view of the disinfection system shown in FIG. 18.
Figure 20:
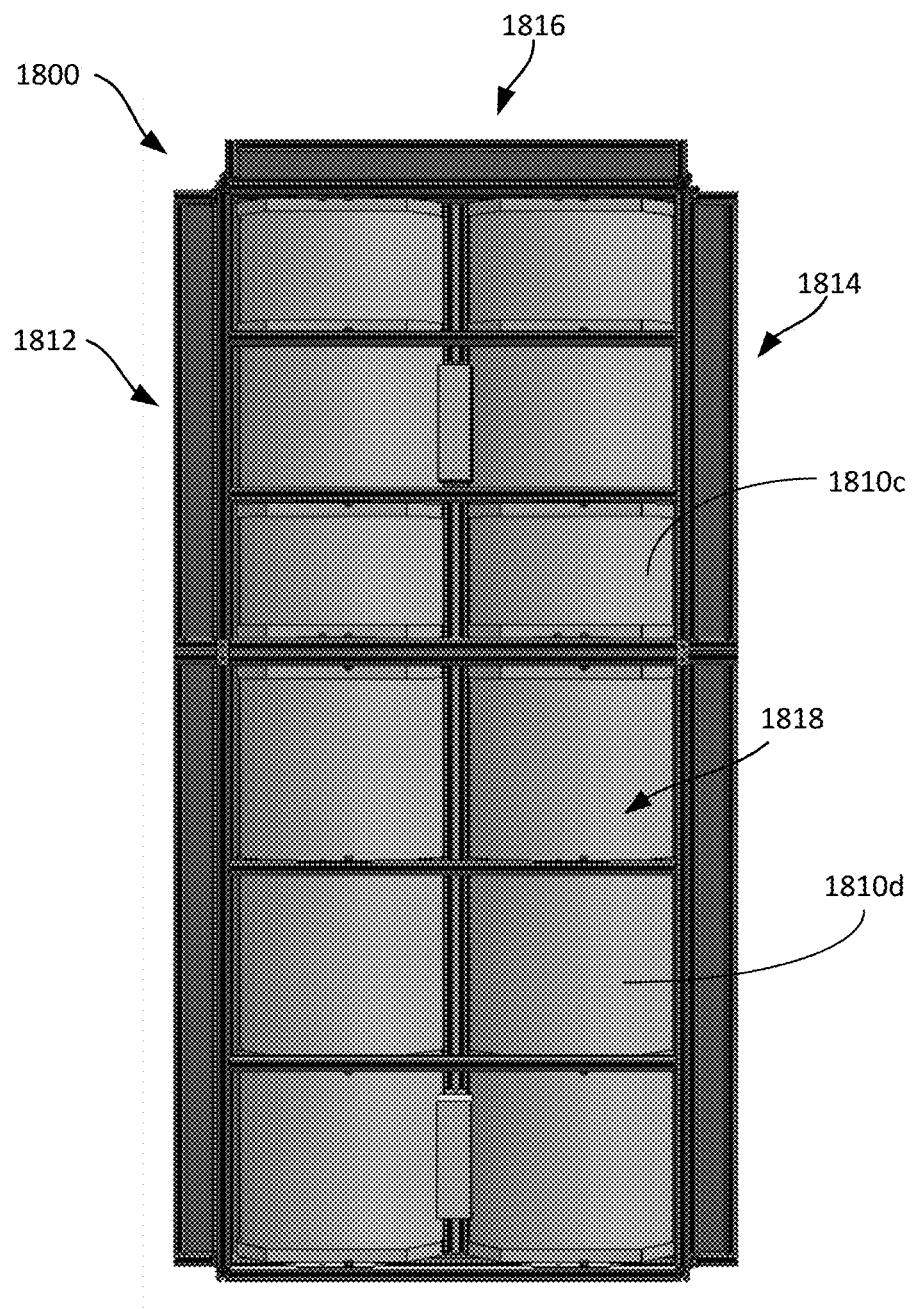
FIG. 20 is a back view of the disinfection system shown in FIG. 18.
Figure 21A:
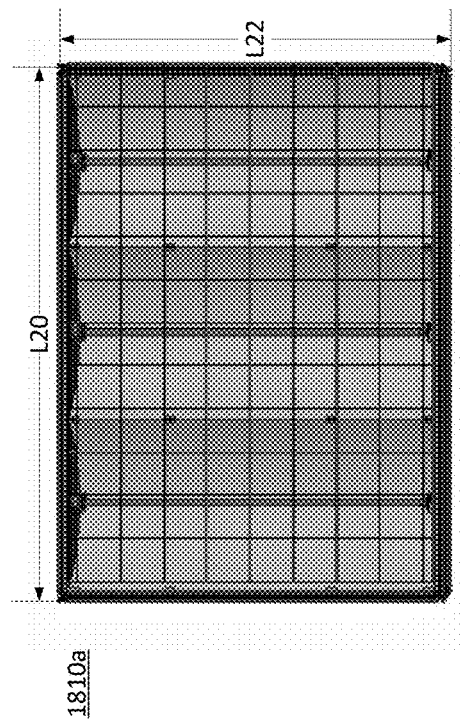
FIGS. 21A-21D depict different modular units of the disinfection system shown in FIG. 18.
Figure 21B:
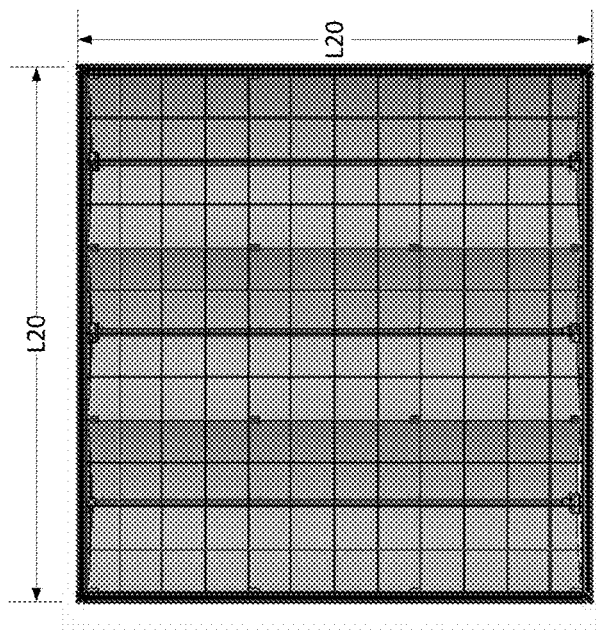
Figure 21C:
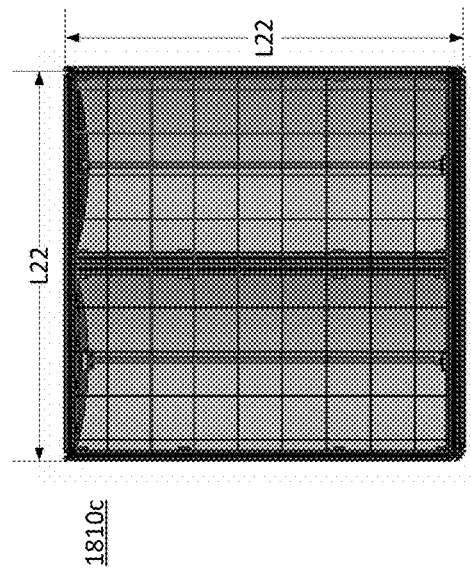
Figure 21D:
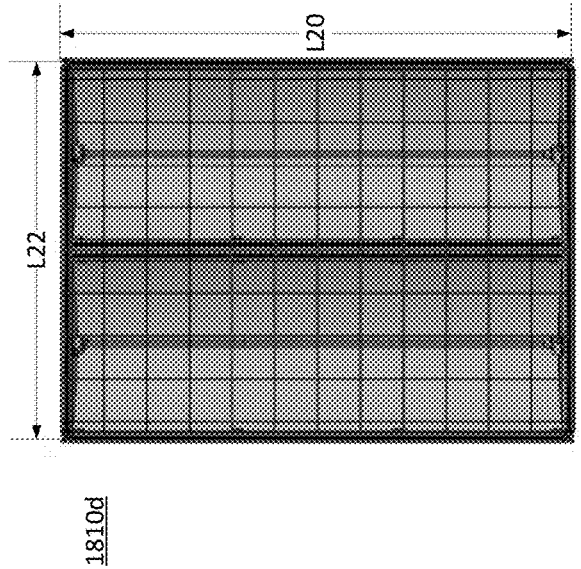

FIGS. 18-20 illustrate different views of an example disinfection system 1800. Disinfection system 1800 can be similar to other disinfection systems described herein (e.g., disinfection systems 100, 200, 700, 800, 900, and/or 1200), and can include components that are structurally and/or functionally similar to the components of those systems. For example, disinfection system 1800 includes a plurality of walls 1812, 1814, 1816, 1818 that define a chamber 1824. Each wall 1812, 1814, 1816, 1818 can be formed of one or more modular units.

Depending on the size requirements of walls 1812, 1814, 1816, 1818, the modular units used to form those walls can have specific dimensions and/or configurations. For example, wall 1812 can be formed of two types of modular units, e.g., a first type of modular unit 1810a and a second type of modular unit 1810b. Wall 1814 can be formed of the same two types of modular units. Wall 1816 can be formed of a single modular unit, e.g., the first type of modular unit 1810a. And wall 1818 can be formed of two types of modular units, e.g., a third type of modular unit 1810c and a fourth type of modular unit 1810d. Altogether, walls 1812, 1814, 1816, 1818 can be formed of four different types of modular units 1810a, 1810b, 1810c, 1810d. While four different types of modular units are depicted in FIG. 18, it can be appreciated that any number of types of modular units can be used to form disinfection systems described herein.

Each of the modular units 1810a, 1810b, 1810c, 1810d can include a set of reflective units or surfaces 1820 and a set of energy sources 1822. Reflective units 1820 and/or energy sources 1222 can be similar to other reflective units and energy sources described herein. For example, each reflective unit 1820 can have a reflective surface that can reflect energy emitted by energy sources 1822 into chamber 1824. As depicted in FIGS. 18-21D, each reflective unit 1820 can have a hyperbolically shaped reflective surface that can be configured to distribute energy emitted by energy sources 1822 and reflect it into chamber 1824. Each energy source 1822 can be disposed within a reflective unit 1820. Energy sources 1822 can include at least one light tube configured to emit disinfecting light (e.g., UV light). Energy sources 1822 can be connected to electrical connectors 1826 disposed within or adjacent to each reflective unit 1820. While not depicted, it can be appreciated that additional reflective units and/or energy sources can be disposed on additional walls or surfaces of disinfection system 1800.

The four types of modular units 1810a, 1810b, 1810c, 1810d can have different dimensions and/or configurations. Each modular unit 1810a, 1810b, 1810c, 1810d can be designed to couple to adjacent modular units via one or more connectors 1825. For example, connectors 1825 can include snap-on components that can mate with one another to connect two modular units together. Alternatively or additionally, connectors 1825 can include fasteners, adhesives, magnets, etc. that can adhere two adjacent modular units to one another. In some embodiments, connectors 1825 can include electrical connections and/or fluid connections, which can connect to electrical connections and/or fluid connections in adjacent modular units such that a network of electrical connections and/or fluid connections can be formed to connect one or more components of modular units 1810a, 1810b, 1810c, 1810d to power source(s), fluid source (s), a control panel, a processor, and/or other centralized elements.

The modular units 1810a, 1810b, 1810c, 1810d are dimensioned such that they fit with one another to form a box-shaped disinfection system 1800. For example, as shown in FIGS. 21A-21D, modular unit 1810a can be L20-by-L22, modular unit 1810b can be L20-by-L20, modular unit 1810c can be L22-by-L22, and modular unit 1810d can be L22-by-L20, such that the modular units 1810a, 1810b, 1810c, 1810d form a chamber 1824 having a length of approximately L20, a width of approximately L22, and a height of approximately L20 and L22. In an embodiment, L20 and L22 can be less than about 50 inches. In an embodiment, L20 can be approximately 48 inches and L22 can be approximately 36 inches. In an embodiment, L20 and L22 are each multiples of a common value (e.g., 12 inches), and are at least equal to or greater than that common value and less than approximately four times that common value. In an embodiment, L20 and L22 can each be at least between approximately 12 and approximately 48 inches. In an embodiment, L20 and L22 can be equal to one another.

While disinfection system 1800 is depicted as being box-shaped (e.g., having a rectangular cross-section), it can be appreciated that other shapes and/or configurations of disinfection system 1800 can be used, e.g., for receiving different sized objections as further described herein.

When disinfection system 1800 forms a chamber 1824 having dimensions of approximately 36-by-48-by-84 inches (e.g., when L20 is approximately 48 inches and L22 s approximately 36 inches) with an opening 1830 of approximately 36-by-84 inches, disinfection system 1800 can be sized to receive medical equipment, such as, for example, wheelchairs, IV poles, medical carts, computer stations, dialysis machines, anesthesia machines, ECG machines, etc. Alternatively, different arrangements and/or types of modular units can be used to accommodate other types of medical equipment. For example, multiple 36-by-36 inch modular units (e.g., modular unit 1810c) can be used to form a smaller enclosure that is 36-by-36-by-36 inches, which can be used to disinfect wheelchairs without IV poles, computer stations, etc. As another example, two 48-by-48 inch modular units can be arranged side-by-side to form the side and top walls of a disinfection unit such that a longer chamber of approximately 96 inches in length can be formed to receive longer equipment such as gurneys.

Disinfection system 1800 can include a bottom wall 1836, as depicted in FIGS. 18 and 19. Bottom wall 1836 can be formed of a signal unitary piece or be formed of multiple pieces that couple together to form a generally flat bottom surface for supporting objects within chamber 1824. The bottom wall 1836 can have a reflective surface (e.g., for further reflecting and directing light energy toward an object being disinfected) or non-reflective surface. In an embodiment, bottom wall 1836 can be a rigid and durable material, e.g., a metal such as stainless steel. The bottom wall 1836 of the disinfection system 1800 can prevent energy and/or disinfecting agent(s) being delivered within chamber 1824 from affecting (e.g., degrading, discoloring) a floor or other surface upon which the disinfection system 1800 is positioned.

Disinfection system 1800 can optionally include a front door or wall (not depicted). For example, similar to other disinfection systems described here, disinfection system 1800 can include a door that is hinged, rolling, folded (e.g., bi-folded), sliding, etc. The front door can be movable between a closed position and an open position. In the closed position, the front door can prevent energy and/or disinfection agent(s) within the chamber 1824 from exiting the chamber and affecting surrounding objects and/or persons. In the open position, the front door can enable an object to be positioned within and/or removed from the chamber 1824.

Figure 22:
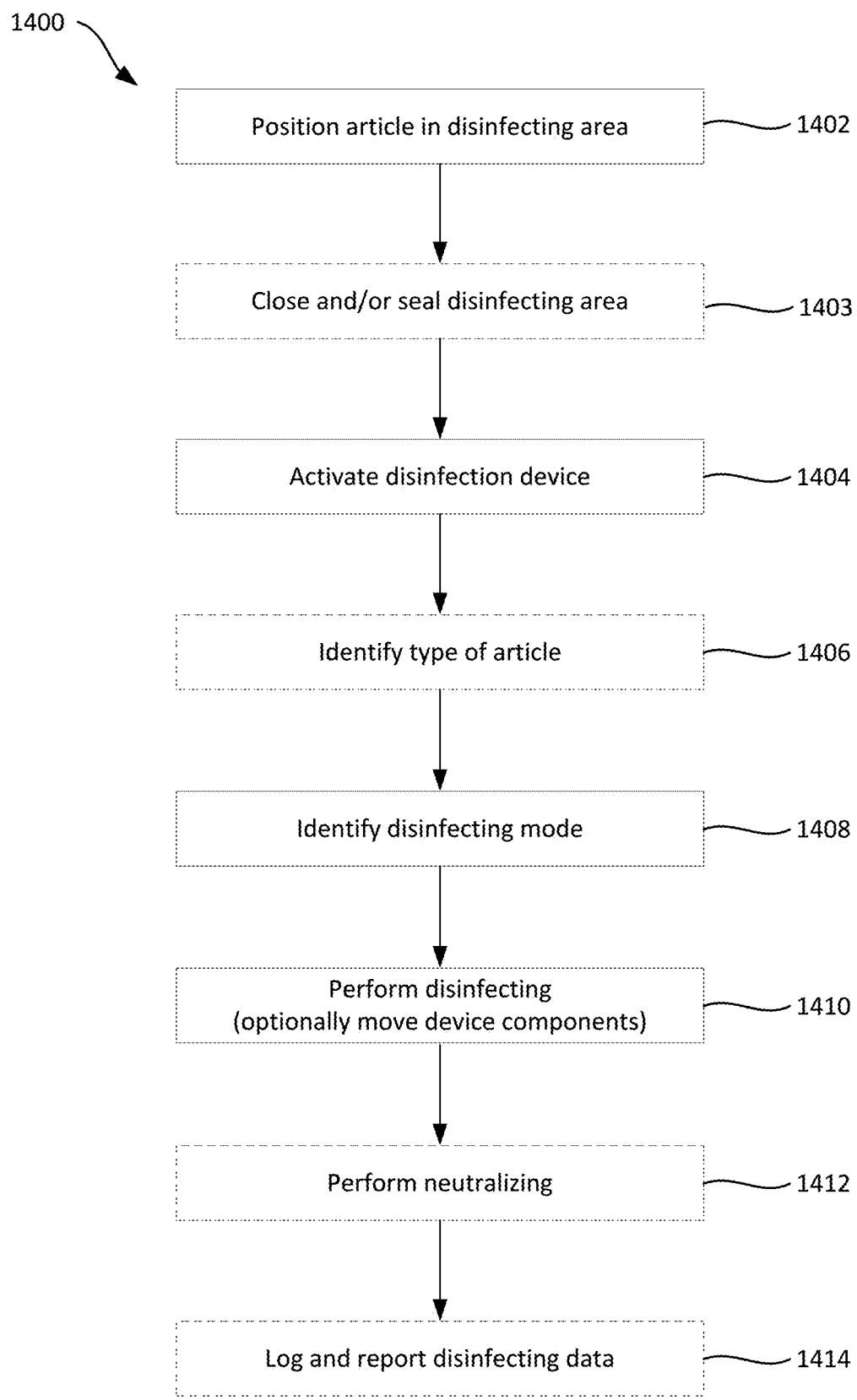
FIG. 22 is a flow chart of a method of disinfecting using a disinfection system, according to embodiments disclosed herein.

FIG. 22 is a flow chart of a method 1400 for disinfecting using a disinfection device, such as any of the disinfection systems disclosed herein. An object or article (e.g., a piece of medical equipment) can be placed in a disinfecting area, at 1402. Disinfecting area can be an open space adjacent to a disinfection device and/or a space within a chamber (e.g., chamber 124, 724, 824, 924, 1224, and/or 1334) defined by a disinfection device. Optionally, the disinfecting area can be closed or sealed, at 1403. The disinfection device can be activated, at 1404. For example, a user can use his badge to turn on and activate the disinfection device. Alternatively, a user located at a remote location can use a control panel to activate the disinfection device. Optionally, at 1406, the disinfection device, e.g., via sensors (e.g., sensor(s) 164) and/or user inputs via a control panel having a user interface (e.g., control panel 150 having I/O interface 152), can identify the type of article, e.g., the type of medical equipment. Based on the type of article that is identified, or based on other information in putted by a user (e.g., via the control panel and/or user interface), the disinfection device can identify a disinfecting mode to use, at 1408.

At 1410, the disinfection device can perform the disinfecting according to the disinfecting mode. In some embodiments, the disinfection mode may involve disinfecting using energy (e.g., UV light and/or pulses of HINS light) and one or more disinfecting agents (e.g., disinfecting agent 190). For example, a set of energy sources capable of emitting energy at an intensity capable of disinfecting a surface of the article can be energized, and at least one disinfecting agent can be delivered to the disinfecting area via a set of spray units.

One or a combination of disinfecting agents may be used: aerosolized or vaporized hydrogen peroxide, aerosolized or vaporized peracetic acid-hydrogen peroxide combination, aerosolized or vaporized electrolyzed water, aerosolized or vaporized cold atmospheric pressure plasma, or aerosolized or vaporized polymeric guanidine. Optionally, prior to and/or during the disinfection process, the disinfection device can move device components (e.g., reflective units, power sources, spray units, exhaust units, sensors, etc.) to perform the disinfection. For example, the disinfection device can move device components to position certain components closer to the article being disinfected, e.g., to increase efficiency and/or efficacy of disinfection. Optionally, at 1412, the disinfection device can perform neutralizing by applying a neutralizing agent (e.g., neutralizing agent 192), to reduce residual disinfecting from degrading the surfaces of the article being disinfecting and/or to reduce the risk of harmful contact of the disinfecting agent with a human after the article is removed from the disinfecting area. Optionally, at 1414, the disinfection device, via sensors, processors, communication channels, etc., can log and/or report disinfecting data, such as, for example, the article that was disinfected, the user initiating the disinfection, etc.

Figure 23:
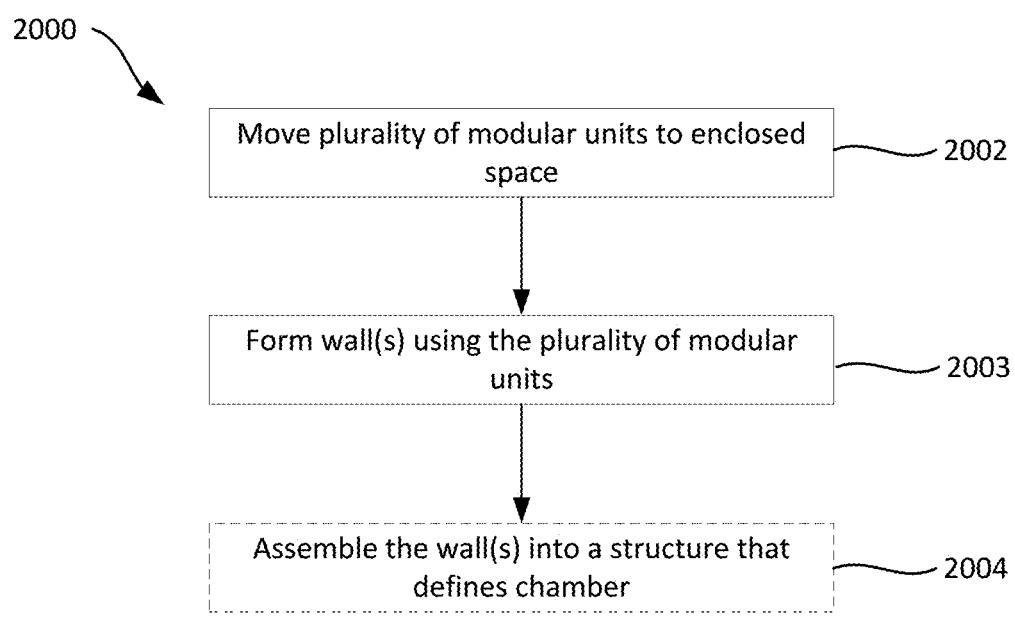
FIG. 23 is a flow chart of a method of assembly a disinfection system, according to embodiments disclosed herein.

FIG. 23 depicts a flow chart of a method 2000 for assembling a disinfection device, such as any of the disinfection systems disclosed herein. A plurality of modular units can be moved from a first location outside of an enclosed space (e.g., a room of a hospital) to a second location inside the enclosed space though an opening (e.g., a doorway), at 2002. Each modular unit can be sized to fit through the opening. The modular units can be assembled into one or more walls or panels, at 2003. Optionally, at 2004, the modular units can be assembled into one or more walls forming a structure that defines a chamber sized to receive an object (e.g., a piece of medical equipment). In some embodiments, the modular units can first be assembled into a plurality of walls, and the plurality of walls can be arranged to form the structure that defines the chamber.

Figure 24:
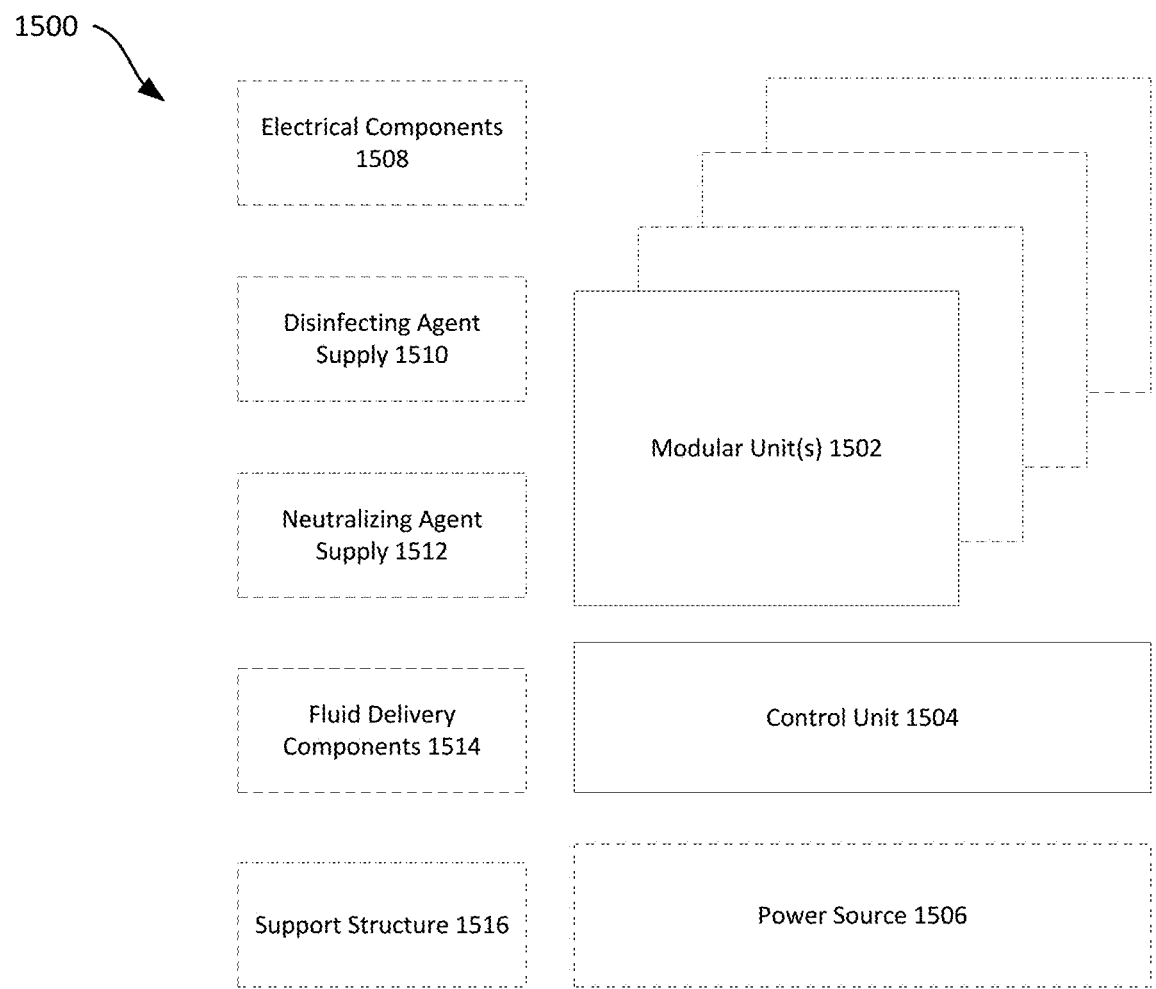
FIG. 24 schematically illustrates a kit including modular units and other components of a disinfection system, according to embodiments disclosed herein.

FIG. 24 depicts various components that can form an example disinfection system 1500. The components depicted in FIG. 24 can be provided in a kit, which can be delivered to an onsite location (e.g., a room in a hospital) for assembly at the onsite location. As shown, the components can include one or more modular unit(s) 1502. Modular unit(s) 1502 can be similar to any of the other modular units disclosed herein, and can include similar components as those modular units. The components can include a control unit 1504, which can be used to control and operate disinfection system 1500, once it is assembled for use. Control unit 1504 can include, for example, a processor (e.g., processor 154) and/or a control panel (e.g., control panel 150). The components can optionally include a power source 1506 and/or electrical component 1508 connecting other components of disinfection system 1500 to the power source 1506 (e.g., modular unit(s) 1502 and/or components included on modular unit(s) 1502, such as energy sources, reflective units, spray units, exhaust units, sensors, etc.). Alternatively, the components provided in the kit do not include a power source, but they include suitable electrical components to connect one or more components of disinfection system 1500 to a remote power source (e.g., via a power port). Optionally, the component can also include a disinfecting agent supply 1510, a neutralizing agent supply 1512, and/or fluid delivery components 1514 for establishing fluid communication between disinfecting agent supply 1510 and/or neutralizing agent supply 1512 to one or more spray units disposed on modular unit(s) 1502. Optionally, the components can also include support structure 1516, for supporting modular unit(s) 1502 in a specific arrangement and/or coupling modular unit(s) 1502 to one another in a specific arrangement.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with values and/or ranges generally refer to those values and/or ranges near to a recited value and/or range. In some instances, the terms "about" and "approximately" may mean within ±10% of the recited value. The terms "about" and "approximately" may be used interchangeably.

The invention claimed is:

1. A kit, comprising:
a plurality of modular units coupleable to one another to form a plurality of walls that collectively define a chamber sized to receive an object, the plurality of walls including a top wall, a back wall, and a set of side walls, the plurality of modular units including:
a first set of modular units coupleable to each other to form a first side wall from the set of side walls, a first modular unit of the first set of modular units being stacked on a second modular unit of the first set of modular units when the first set of modular units are coupled to each other such that the first side wall has a height that is greater than one modular unit from the first set of modular units;
a second set of modular units coupleable to each other to form a second side wall from the set of side walls, a first modular unit of the second set of modular units being stacked on a second modular unit of the second set of modular units when the second set of modular units are coupled to each other such that the second side wall has a height that is greater than one modular unit from the second set of modular units; and a third set of modular units coupleable to each other to form at least one of the top wall or the back wall, a first modular unit of the third set of modular units being stacked on a second modular unit of the third set of modular units when the third set of modular units are coupled to each other such that the third side wall has a height that is greater than one modular unit from the third set of modular units; and a plurality of energy sources including at least one energy source disposed on each modular unit from the plurality of modular units, a set of energy sources from the plurality of energy sources configured to provide energy having an intensity configured to disinfect a surface of the object when the object has been received within the chamber.

2. The kit of claim 1, further comprising a plurality of reflective surfaces including at least one reflective surface disposed on each modular unit from the plurality of modular units, each reflective surface from the plurality of reflective surfaces configured to reflect energy provided by at least one energy source from the plurality of energy sources, such that the energy can be directed toward the object when the object has been received within the chamber.

3. The kit of claim 1, wherein each modular unit from the plurality of modular units has a length that is less than a maximum length of the object.

4. The kit of claim 1, wherein each modular unit from the plurality of modular units has a width ranging from approximately 10 to approximately 50 inches and a length ranging from approximately 10 to approximately 50 inches.

5. The kit of claim 1, wherein each modular unit from the plurality of modular units has a width of at least approximately 12 inches and a length of no more than approximately 48 inches.

6. The kit of claim 1, wherein each wall from the plurality of walls has a width and a length that are multiples of a common value.

7. The kit of claim 1, wherein:
the first set of modular units includes four modular units coupleable to each other to form the first side wall,
the second set of modular units includes four modular units coupleable to each other to form the second side wall,
the third set of modular units includes four modular units coupleable to each other to form the top wall, and
the plurality of modular units further including a fourth set of modular units including two modular units couplable to each other to form the back ball.

8. The kit of claim 1, wherein the energy source includes at least one of: a mercury vapor light source, a xenon gas light source, a light emitting diode (LED), or a light emitting nanoparticle.

9. The kit of claim 1, wherein the energy source includes a light source capable of emitting ultraviolet (UV) light having a wavelength of approximately 200 nm to approximately 280 nm.

10. The kit of claim 1, further comprising:
a fluid dispenser configured to dispense a disinfecting agent into the chamber; and
an exhaust unit configured to vent the disinfecting agent out from the chamber.

11. The kit of claim 10, wherein the fluid dispenser is disposable on at least one modular unit from the plurality of modular units.

12. The kit of claim 10, wherein the disinfecting agent includes at least one of:
hydrogen peroxide, peracetic acid, electrolyzed water, atmospheric pressure plasma, polymeric guanidine, or ozone.

13. The kit of claim 10, wherein the fluid dispenser is further configured to dispense a neutralizing agent, after dispensing the disinfecting agent, to reduce degradation caused by the disinfecting agent.

14. The kit of claim 1, wherein each modular unit from the plurality of modular units has a surface that is configured to cooperatively engage a surface of at least one other modular unit from the plurality of modular units such that a seal is formed between that modular unit and the at least one other modular unit, the seal configured to prevent energy emitted by at least one energy source from the plurality of energy sources from exiting the chamber.

15. The kit of claim 1, further comprising a power source configured to supply power to the plurality of energy sources.

16. The kit of claim 15, wherein each modular unit from the plurality of modular units includes an electrical connector configured to connect, via an electrical path, to the power source, such that the power source can supply power to the at least one energy source disposed on that modular unit.

17. The kit of claim 16, wherein the electrical connector of that modular unit is disposed on at least one of:
an edge of that modular unit and is configured to couple to an electrical connector of another modular unit from the plurality of modular units;
a surface of that modular unit facing an interior of the chamber; or
a surface of that modular unit external to the chamber.

18. The kit of claim 1, further comprising a transport unit disposable within the chamber, the transport unit configured to move the object into the chamber to be disinfected by the set of energy sources and to move the object out of the chamber after being disinfected by the set of energy sources.

19. The kit of claim 1, further comprising at least one foldable panel section configured to function as a door into the chamber, the at least one foldable panel section transitionable between an open configuration in which the object can be received into the chamber and a closed configuration in which the chamber is sealed from a surrounding environment.

20. An apparatus, comprising:
a plurality of walls collectively defining a chamber sized to receive an object, at least three walls from the plurality of walls each formed of a plurality of modular units, the plurality of walls including a top wall, a back wall, and a set of side walls, each modular unit from the plurality of modular units coupleable to at least two other modular units from the plurality of modular units, such that each wall of the plurality of walls has a height greater than a height of one of the modular units; and
a plurality of energy sources including at least one energy source disposed on each modular unit from the plurality of modular units, a set of energy sources from the plurality of energy sources configured to provide energy having an intensity capable of disinfecting a surface of the object when the object has been received within the chamber.

* * * * *